(12) United States Patent
Yamamoto et al.

(10) Patent No.: US 8,906,234 B2
(45) Date of Patent: Dec. 9, 2014

(54) FILTER DEVICE

(75) Inventors: Takeki Yamamoto, Hyogo (JP);
Masaya Nakatani, Hyogo (JP); Takuya Oka, Kyoto (JP); Takahiro Nogami, Osaka (JP)

(73) Assignee: Panasonic Corporation, Osaka (JP)

( * ) Notice: Subject to any disclaimer, the term of this patent is extended or adjusted under 35 U.S.C. 154(b) by 11 days.

(21) Appl. No.: 13/616,763

(22) Filed: Sep. 14, 2012

(65) Prior Publication Data

US 2013/0001149 A1 Jan. 3, 2013

Related U.S. Application Data

(63) Continuation-in-part of application No. PCT/JP2011/005296, filed on Sep. 21, 2011.

(30) Foreign Application Priority Data

Sep. 24, 2010 (JP) ................................. 2010-213496
Apr. 1, 2011 (JP) ................................. 2011-081453

(51) Int. Cl.
*B01D 61/18* (2006.01)
*B01L 3/00* (2006.01)
*G01N 33/18* (2006.01)
*B01D 39/06* (2006.01)

(52) U.S. Cl.
CPC ........... *B01D 39/06* (2013.01); *B01L 3/502707* (2013.01); *B01L 3/502753* (2013.01); *G01N 33/1826* (2013.01); *B01D 2239/1208* (2013.01); *B01L 2200/027* (2013.01); *B01L 2300/0681* (2013.01); *B01L 2300/087* (2013.01); *B01L 2400/0406* (2013.01); *G01N 33/18* (2013.01)
USPC .................... 210/321.6; 210/321.75; 210/505; 422/535

(58) Field of Classification Search
CPC ............ B01D 39/06; B01D 2239/1208; B01L 2200/027; B01L 2300/0681; B01L 2300/087; B01L 2400/0406; B01L 3/5025; B01L 3/502707; B01L 3/502753; G01N 33/18; G01N 33/1826; B81B 2201/0214; B81B 2201/052; B81B 2201/10
USPC ........ 210/600, 323.1, 435, 500.1, 502.1, 503, 210/504, 505, 507, 508, 509, 510.1, 789; 422/48, 534, 535, 407, 412, 417, 420, 422/422, 427
See application file for complete search history.

(56) References Cited

U.S. PATENT DOCUMENTS 4,167,482 A * 9/1979 Muller ......................... 210/791
6,227,009 B1 5/2001 Cusick et al.
(Continued)

FOREIGN PATENT DOCUMENTS

JP  02-284615   11/1990
JP  11-012180   1/1999
(Continued)

OTHER PUBLICATIONS

Xinhua Zong, Kwangsok Kim, Dufei Fang, Shaofeng Ran, Benjamin S Hsiao, Benjamin Chu, Structure and process relationship of electrospun bioabsorbable nanofiber membranes, Polymer, vol. 43, Issue 16, Jul. 2002, pp. 4403-4412.*

(Continued)

*Primary Examiner* — David C Mellon
*Assistant Examiner* — Pranav Patel
(74) *Attorney, Agent, or Firm* — McDermott Will & Emery LLP

(57) ABSTRACT

A filter device of the present disclosure includes a first port from which a solution containing a substance is to be input, and a first flow passage communicating with the first port. A filter portion made of a plurality of fibrous substances including inorganic oxide is formed in at least one part in the first flow passage. The plurality of fibrous substances has one peak in the diameter distribution.

24 Claims, 23 Drawing Sheets

(56) References Cited

U.S. PATENT DOCUMENTS

| | | | |
|---|---|---|---|
| 6,267,898 B1 | 7/2001 | Fukuda et al. | |
| 2001/0012612 A1 | 8/2001 | Petersen et al. | |
| 2001/0027946 A1 | 10/2001 | Fukuda et al. | |
| 2003/0119034 A1 | 6/2003 | Kang et al. | |
| 2004/0149659 A1* | 8/2004 | Kane | 210/649 |
| 2004/0197898 A1* | 10/2004 | Nakatani et al. | 435/287.1 |
| 2004/0253691 A1* | 12/2004 | Nakatani | 435/101 |
| 2005/0038498 A1 | 2/2005 | Dubrow et al. | |
| 2005/0106552 A1 | 5/2005 | Ikeda | |
| 2006/0029923 A1* | 2/2006 | Togawa et al. | 435/2 |
| 2009/0152110 A1* | 6/2009 | Hiraoka et al. | 204/403.01 |
| 2009/0181441 A1* | 7/2009 | Jin et al. | 435/180 |
| 2010/0219488 A1 | 9/2010 | Nakatani et al. | |
| 2011/0232794 A1 | 9/2011 | Nakatani et al. | |

FOREIGN PATENT DOCUMENTS

| | | |
|---|---|---|
| JP | 11-012181 | 1/1999 |
| JP | 2000-211940 | 8/2000 |
| JP | 2002-239317 | 8/2002 |
| JP | 2003-522521 | 7/2003 |
| JP | 2003-315349 | 11/2003 |
| JP | 2004-325304 | 11/2004 |
| JP | 2007-178366 | 7/2007 |
| JP | 2007-526439 | 9/2007 |
| JP | 2008-275627 | 11/2008 |
| WO | WO 2009/034697 | 3/2009 |
| WO | WO 2009/037784 A1 | 3/2009 |
| WO | WO 2010/082279 A1 | 7/2010 |

OTHER PUBLICATIONS

English language machine translation of JP 2000-211940.*
English language machine translation of JP 2007-526439.*
International Search Report issued in International Patent Application No. PCT/JP2011/005296 dated Dec. 27, 2011.

* cited by examiner 1.00μm

DIAMETER OF FIBROUS SUBSTANCE
(nm)

5.00μm

FILTER DEVICE

This application is a Continuation-in-Part of International Application No. PCT/JP11/005296, filed on Sep. 21, 2011, claiming priority of Japanese Patent Application No. 2010-213496, filed on Sep. 24, 2010 and Japanese Patent Application No. 2011-081453, filed on Apr. 1, 2011, the entire contents of each of which are hereby incorporated by reference.

TECHNICAL FIELD

The present disclosure relates to a filter device used for extracting only a specific substance from a solution.

BACKGROUND ART

Separation of only a specific substance (specimen) from a sample test material containing a plurality of substances is required in various fields. However, in particular, when the presence rate of the specific substrate is low, it is difficult to detect only the specific substance from the sample test material containing the other substances.

One example of a conventional filter device is manufactured by the following process. The surface of the first substrate made of quartz is subjected to chemical treatment such as dry etching or wet etching, or the process treatment by energy ray irradiation treatment with laser, ion beam, or the like, so that a plurality of island-shaped columnar products are formed. Thereafter, a second substrate is joined to the columnar products so as to seal the columnar products. Thus, a space in the island-shaped columnar product sealed by the first substrate and the second substrate is used as a filter flow passage.

Furthermore, in another example of the conventional filter device, a device includes a flow channel on a surface of a first substrate in which a plurality of fibrous layers including fibrous protruding portions are provided in the flow channel and extend to opening portions.

One exemplary use of such a filter device is filtration of leukocyte from erythrocyte in blood. The erythrocyte has the diameter from 7 µm to 8 µm, and can enter and pass through a capillary blood vessel whose diameter is not larger than a half of the diameter of the erythrocyte itself. The leukocyte has a spherical shape whose diameter is from 6 µm to 30 µm, and has smaller deformation ability than flat-shaped erythrocyte. Thus, when the pore size of a filter device is from 3 µm to 6 µm, only the erythrocyte can be allowed to pass.

As one example of a filter device for blood filtration, a leukocyte removing material was disclosed. The leukocyte removing material includes not less than 0.5 wt % and less than 50 wt % of ultra fine fibers whose fiber diameter is not less than 0.02 µm and less than 0.8 µm in which the ultra fine fibers form a mesh structure having circularity of not more than 1.7 and a converted diameter of a circle of not less than 1 µm and less than 20 µm.

Furthermore, in another leukocyte removing device, the leukocyte removing material includes not less than 5 wt % and less than 20 wt % of ultra fine fibers whose fiber diameter is not less than 0.1 µm and less than 0.6 µm in which the ultra fine fiber has a curvature of not less than 1.2.

However, in particular, it is difficult to extract only a specified specimen from a small amount of solution containing many substances.

SUMMARY

A filter device according to the present disclosure includes a first port from which a solution containing a substance is to be input, and a first flow passage communicating with the first port. At least a part of the first flow passage includes a filter portion made of fibrous substances including inorganic oxide. The plurality of fibrous substances has one peak (maximum frequency value) in the diameter distribution.

The present disclosure can provide a filter device having a high filtering rate, and capability of selectively extracting an extracted product and being easily used.

DETAILED DESCRIPTION OF THE PREFERRED EMBODIMENT

First Exemplary Embodiment

Figure 1:
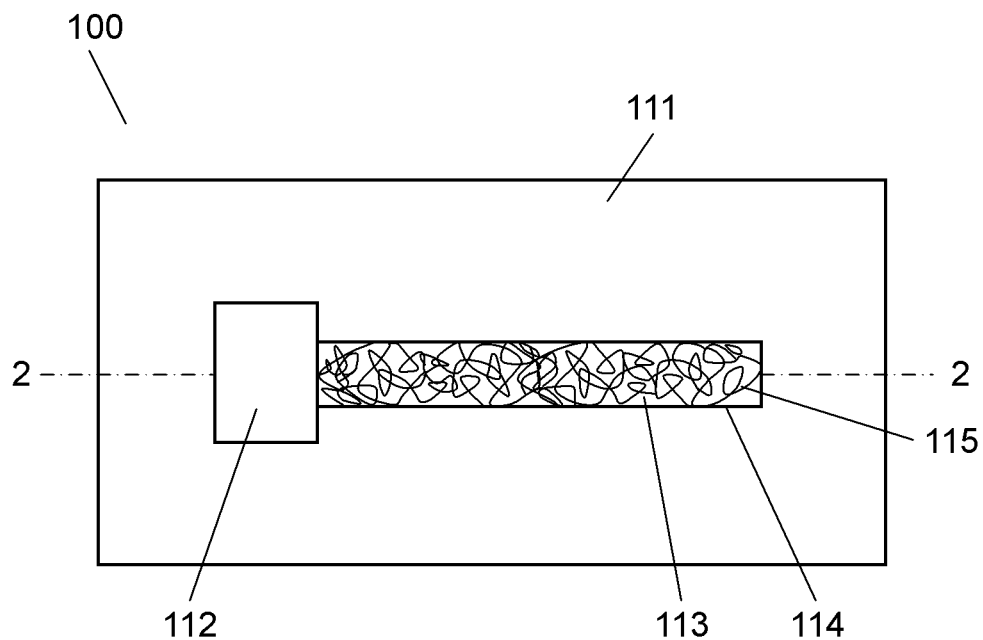
FIG. 1 is a top view of a filter device in accordance with a first exemplary embodiment of the present disclosure.

Hereinafter, a filter device in accordance with a first exemplary embodiment of the present disclosure is described. In each exemplary embodiment, the same reference numerals are given to the same configurations as in preceding exemplary embodiments and detailed description thereof may be omitted. Furthermore, the present disclosure is not necessarily limited to the following exemplary embodiments.

Figure 2:
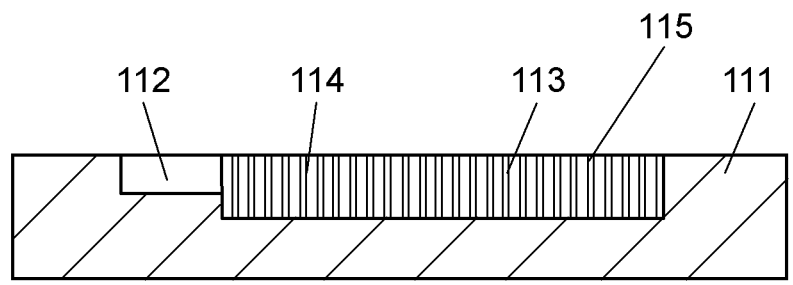
FIG. 2 is a sectional view of the filter device taken on line 2-2 in FIG. 1.
Figure 3:
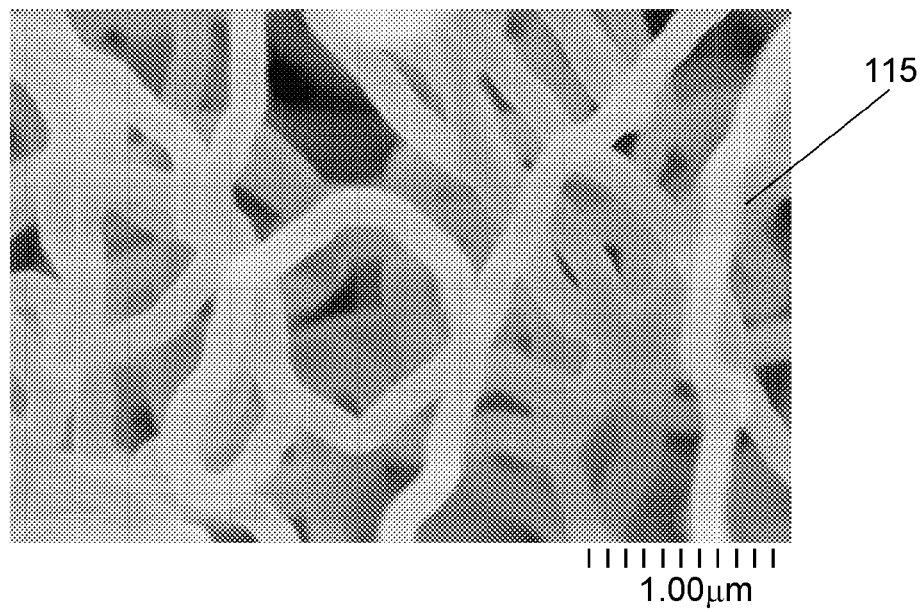
FIG. 3 is an enlarged SEM (scanning electron microscope) photograph of a part of the filter device in accordance with the first exemplary embodiment.

FIG. 1 is a top view of a filter device in accordance with this exemplary embodiment, FIG. 2 is a sectional view of the filter device taken on line 2-2 in FIG. 1, and FIG. 3 is an enlarged SEM photograph of a part of the filter device in accordance with this exemplary embodiment. As shown in FIG. 1, filter device 100 of this exemplary embodiment includes first port 112 and first flow passage 113. First port 112 is a port which is formed on substrate 111 and from which a solution containing a target substance is to be input. First flow passage 113 communicates with first port 112. Furthermore, as shown in FIG. 2, first flow passage 113 includes filter portion 114 for separating a specific component from the solution that contains the target substance and flows from first port 112. Filter portion 114 is, for example, a filter for separating erythrocyte from "a solution derived from a living body and containing whole blood or erythrocyte" (hereinafter referred to as "a blood solution"). Filter portion 114 is made of a plurality of fibrous substances 115 including inorganic oxide. As shown in FIG. 3, the diameters of fibrous substances 115 are substantially uniform. In filter portion 114, a plurality of fibrous substances 115 are entangled with each other, thereby forming gaps. Filter portion 114 may be formed throughout first flow passage 113.

Filter portion 114 includes a plurality of fibrous substances 115 that are entangled with each other. Thus, solid substances, whose maximum diameters are larger than the gaps in fibrous substances 115 among solid substances contained in a solution, are captured as a filtration product by fibrous substances 115. Then, substances which are smaller than the gaps can pass, as a specimen, through fibrous substances 115. Thus, filter portion 114 can separate between the specimen and the filtration product in the solution. However, even when substances are larger than the gaps in fibrous substances 115, they can be extracted as specimens if the specimens (solute) can be easily deformed.

Figure 4:
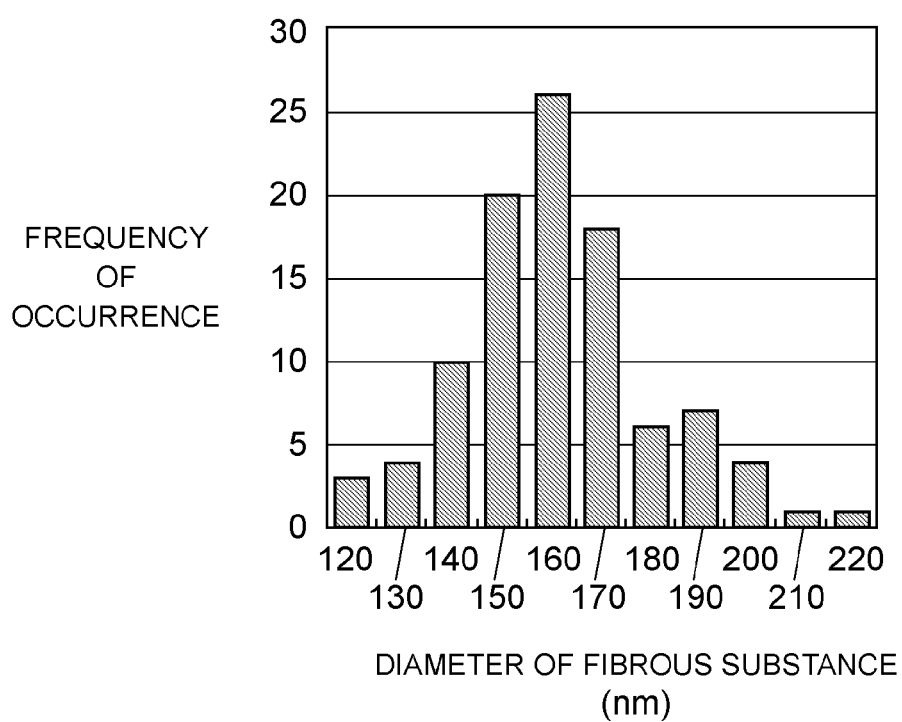
FIG. 4 is a graph showing diameter distribution of fibrous substances of the filter device in accordance with the first exemplary embodiment.

FIG. 4 is a graph showing diameter distribution of fibrous substances of the filter device in accordance with this exemplary embodiment. The diameter distribution of fibrous substances 115 is obtained by measuring fibrous substances 115 by using a scanning electron microscope.

As shown in FIG. 4, fibrous substances 115 have only one peak in the diameter distribution near 160 nm diameter, have a small variation in the diameters, and do not contain a plurality of fibrous substances 115 having largely different diameters.

Furthermore, in this way, when the diameters of fibrous substances 115 are substantially constant, areas of the gaps in filter portion 114 are also uniform. Therefore, when the diameters of fibrous substances 115 are controlled as shown in FIG. 4, any positions in filter portion 114 have a stable and uniform filtering effect. The standard deviation σ of the diameter of the plurality of fibrous substances 115 is calculated by FIG. 4. The diameter distribution of the plurality of fibrous substances 115 is continuous normal distribution, and the range of the diameters of the plurality of fibrous substances 115 is less than twice the standard deviation of the diameters of the plurality of fibrous substances 115. It is more preferable that the range of the diameters of the plurality of fibrous substances 115 is less than the standard deviation of the diameters of the plurality of fibrous substances 115.

It is also preferable to make a CV value (=σ/average×100) of fibrous substance 115 equal to or less than 50%. To do so, since appearance frequency of fibers having a diameter twice or more the minimum diameter becomes small, the variation in the diameter distribution becomes small, thereby making the areas of the gaps uniform.

It is also preferable to make the CV value of fibrous substance 115 close to a CV value of the target substance. It is more preferable to make the CV value of fibrous substance 115 smaller than the CV value of the target substance.

For example, substance coming from living bodies has a CV value of 20% or less. The CV value of erythrocyte is usually 10-20%. Thus, when filter device 100 is used to extract erythrocyte from the blood solution, the CV value of fibrous substance should be less than that of the erythrocyte. To do so, since the erythrocyte can pass any gap of the filter, it improves selectivity of filtration.

When fibrous substances have largely different diameters, that is, thick fibrous substances and thin fibrous substances are mixed with each other to form the filter portion, and when these thick and thin fibrous substances are not evenly mixed, large and small gaps may be mixed. When such large gaps are continuously present, separation property is deteriorated. However, when filter portion 114 is made of extremely fine fibrous substances 115 in which the diameters are substantially uniform, continuously communicating large gaps are not formed. As a result, the gaps having a uniform size can be formed.

Figure 5:
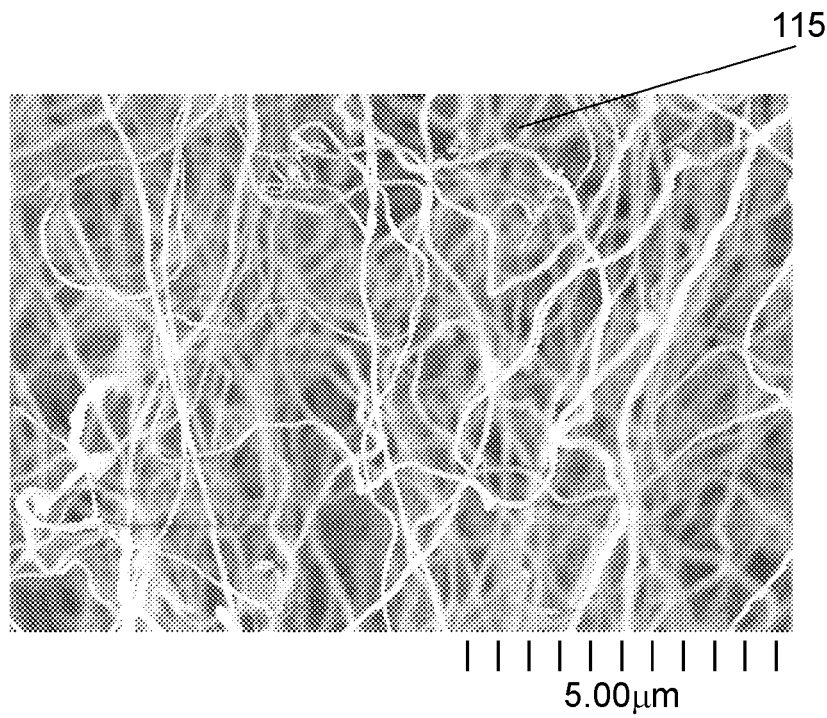
FIG. 5 shows an enlarged SEM photograph of a part of the filter device in accordance with the first exemplary embodiment.

FIG. 5 shows an SEM photograph of a part of the filter device in accordance with this exemplary embodiment. As shown in FIGS. 3 and 5, fibrous substances 115 respectively bend and are entangled with each other, and thereby filter portion 114 is formed such that gaps from various directions are easily covered in first flow passage 113. Furthermore, filter portion 114 is formed in which fibrous substances 115 having a high aspect ratio are closely gathered in such a manner that they are entangled with each other. Therefore, fibrous substances 115 have gaps in various directions. Thus, filtration products from various angles can be adsorbed, and the reliability of filter device 100 can be improved.

A plurality of fibrous substances 115 are not limited to a configuration in which they are closely gathered in such a manner that they are entangled with each other. Fibrous substances 115 may be formed in such a manner that one fibrous substance 115 that is bent and partially formed in a round shape is mixed. Such a structure improves the strength of filter portion 114.

As shown in FIG. 5, fibrous substances 115 include a substance having a plurality of bending portions, in particular, acute-angled bending portions, and a coil shape. When fibrous substance 115 has such a structure, a filtration product can be captured in the bending portion.

Figure 6:
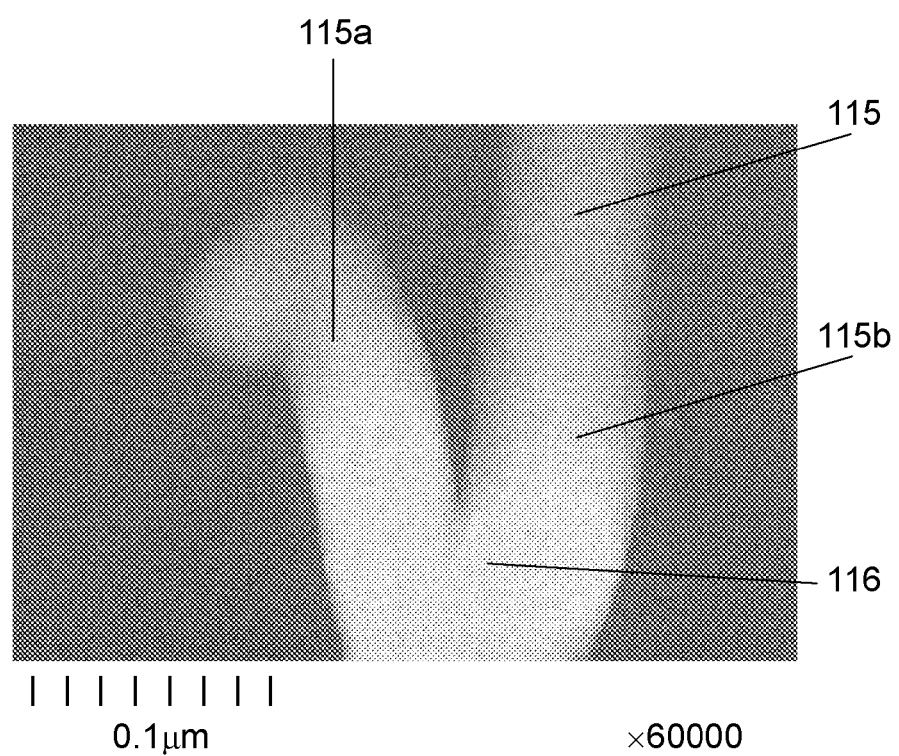
FIG. 6 shows an enlarged SEM photograph of a part of the filter device in accordance with the first exemplary embodiment.

FIG. 6 is an enlarged SEM photograph of a part of the filter device in accordance with this exemplary embodiment. As shown in FIG. 6, it is preferable that a fibrous substance 115 is branched so as to form branched portion 116. In particular, it is preferable that fibrous substances 115 form branched portions in a plurality of directions. Such a structure allows branched portion 116 to capture a filtration product.

As set forth above, plurality of fibrous substances 115 are not limited to a configuration in which they are closely gathered in such a manner that they are entangled with each other, but may be formed in such a manner that they include branched portions in any free directions. A plurality of fibrous substances 115 are entangled with each other or branched, so that filter portion 114 made of a plurality of fibrous substances 115 is firmly formed.

Furthermore, as shown in FIG. 6, it is preferable that an acute-angled gap made by fibrous substance 115a and fibrous substance 115b grown from branched portion 116 is formed such that the surface of the gap is formed facing the upstream direction of first flow passage 113 (direction of first port 112 in FIG. 1). According to the above-mentioned configuration, a filtration product flowing in first flow passage 113 is easily captured by the acute-angled gap, and the filtering effect can be improved.

Figure 7A:
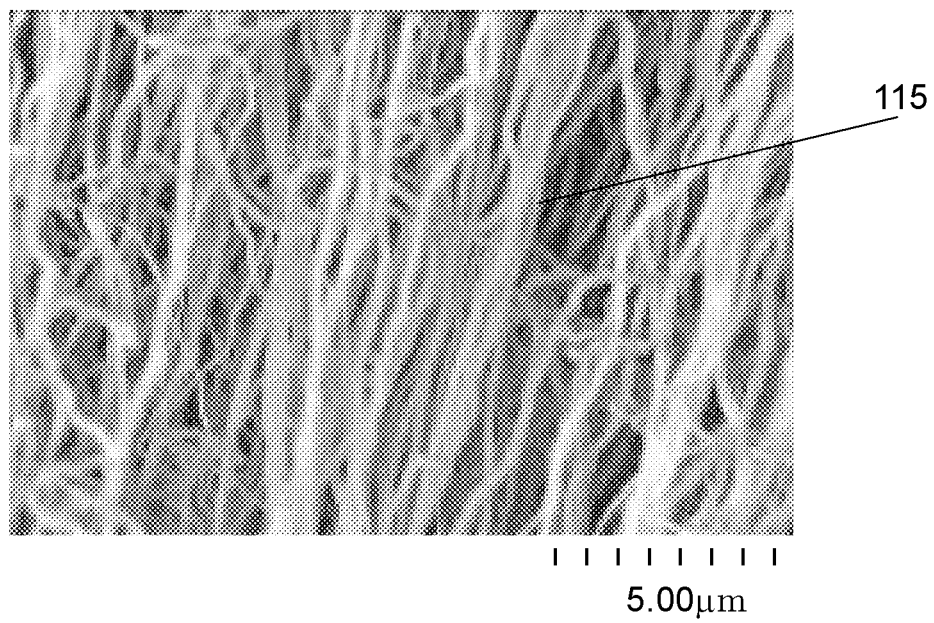
FIG. 7A shows an enlarged SEM photograph of a part of the filter device in accordance with the first exemplary embodiment.
Figure 7B:
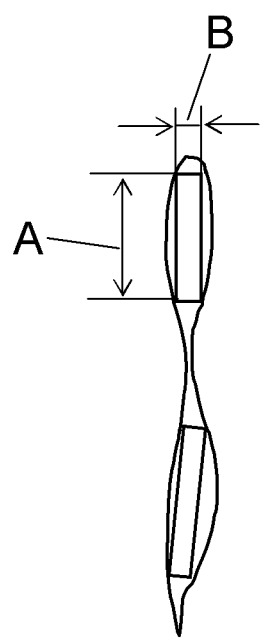
FIG. 7B is a view showing an example of a shape of a gap in a filter portion in accordance with the first exemplary embodiment.

FIG. 7A shows an enlarged SEM photograph of a part of the filter device in accordance with this exemplary embodiment and FIG. 7B is an illustration showing another example of a shape of a gap of a filter portion in accordance with this exemplary embodiment.

As shown in FIG. 7A, it is preferable that the aspect ratio of a gap made by one fibrous substance 115 and another fibrous substance 115 is large. The calculation of the aspect ratio of the gap is carried out by reading out a two-dimensional shape of the gap made by fibrous substances 115 by using a device such as an image analysis device. Then, as shown in FIG. 7B, a quadrangle in which an area in the gap becomes the largest is read out. When the longer side is denoted by "A" and the shorter side is denoted by "B," "A/B" can be calculated as the aspect ratio. When an inner peripheral line of the adjacent gap is not more than 100 nm, a specimen cannot be allowed to pass. In this case, the space is supposed to be a closed space. Furthermore, the length of B is required to be not shorter than 500 nm.

For example, when filter device 100 is used so that a blood solution is used as a solution and the erythrocyte is extracted as a subject specimen, only erythrocyte having a flat shape and much deformation ability as compared with a spherical-shaped leukocyte can pass through the gap having a high aspect ratio. Therefore, the gap made by one fibrous substance 115 and another fibrous substance 115 preferably has shapes such as an ellipse or a rectangle whose aspect ratio is larger than 1 rather than shapes such as a circle or a square whose aspect ratio is near 1. When the gap is formed in such a shape, the leukocyte and the erythrocyte can be separated from each other reliably. More preferably, the gap made by one fibrous substance 115 and another fibrous substance 115 has an aspect ratio of not less than 2.

It is desirable that the size of the gap made by one fibrous substance 115 and another fibrous substance 115 in filter portion 114 is 3 µm to 6 µm. For example, the erythrocyte has the diameter from 7 µm to 8 µm, and can enter and pass through a capillary blood vessel whose diameter is not larger than a half of the diameter of the erythrocyte itself. The leukocyte has a spherical shape whose diameter is from 6 µm to 30 µm, and has smaller deformation ability than flat-shaped erythrocyte. When filter device 100 is used such that a blood solution is used as a solution and the erythrocyte is extracted as a subject specimen, in a region in which the size of the gap is from 3 µm to 6 µm, only the erythrocyte can be allowed to pass. It is not preferable that the size of the gap is larger than 6 µm because leukocyte also passes through filter portion 114.

Fibrous substance 115 provided in first flow passage 113 includes, for example, inorganic oxides such as silicon oxide, titanium dioxide, aluminum oxide, magnesium oxide, tin oxide, and zinc oxide, and the thickness of each fibrous substance is about 0.01 µm to 1 µm. When fibrous substance 115 includes inorganic oxide, it is excellent in heat resistance property and chemical resistance property. Therefore, it can be used at temperatures and for drugs which polymer materials cannot tolerate.

Fibrous substance 115 includes oxides containing silicon oxide as a main component, and preferably includes amorphous-state silicon dioxide. Since the amorphous-state silicon dioxide has higher flexibility as compared with fibrous substances including single crystal silicon dioxide, they are not easily broken.

Furthermore, since silicon dioxide is a material that has high compatibility with a living body and is chemically and thermally stable, it can be easily subjected to surface treatment.

Furthermore, silicon dioxide is chemically stable. Applying of a reagent to filter portion 114 may be carried out together with treatment with an organic solvent or drying treatment at high temperatures. When filter portion 114 is made of a fibrous material including silicon dioxide having excellent chemical resistance property, reagents with various properties can be applied. Furthermore, since silicon dioxide are excellent in the heat resistance property, the shape of filter portion 114 is not melted and broken during treatment at high temperatures. Thus, since fibrous materials including silicon dioxide are more excellent in the chemical resistance property and the heat resistance property as compared with fibrous materials including an organic polymer, they have advantageous that application and fixation of adsorbent materials can be easily carried out.

The Young's modulus (modulus of longitudinal elasticity) that is one of the physical values representing that silicon dioxide cannot be easily deformed is about 30 GPa to 75 GPa, which is higher than the Young's modulus of polymer, 0.01 GPa to 5 GPa. Therefore, even if external force such as flowing of a solution is applied, the material is not easily deformed, and therefore the structure of a gap can be maintained during filtering. As a result, stable filtering that does not depend upon the flow speed of the solution can be carried out.

Herein, first port 112 and first flow passage 113 are provided by forming channels on substrate 111 by fine processing such as an etching process. Substrate 111 can be formed of inorganic materials such as glass, silicon, thermal oxidation $SiO_2$, polysilicon, and amorphous silicon. Alternatively, substrate 111 can be also formed of resin such as polydimethylsiloxane (PDMS), polypropylene, polycarbonate, polyolefin, polystyrene, polyamide, polymethylmethacrylate (PMMA), and cyclic polyolefin, and a composite material of such resin and glass. Furthermore, when substrate 111 is formed of a hydrophobic material, substrate 111 is preferably subjected to surface treatment such as treatment for making substrate 111 hydrophilic.

The width of first flow passage 113 can be adjusted appropriately in order to extract the target material. When filter device 100 of this exemplary embodiment is used for separating and extracting erythrocyte from a blood solution, it is preferable that the width of first flow passage 113 is about 10 to 100 μm from the viewpoint of rapidity of extraction of erythrocyte.

The following is a description of a method of extracting erythrocyte from a blood solution by using filter device 100 in this exemplary embodiment.

When the blood solution as a sample is input into first port 112, the input blood solution gradually flows in first flow passage 113. When the whole blood flows in filter portion 114 in first flow passage 113, the leukocyte is captured in a position near first port 112 of first flow passage 113. Herein, in filter portion 114, gaps having a size of 3 μm to 6 μm are made by a plurality of fibrous substances 115 including inorganic oxide and having one peak in the diameter distribution. On the other hand, the erythrocyte gradually flows through first flow passage 113, and finally remains in first flow passage 113 in a state in which it is separated from the leukocyte. As a result, the erythrocyte and the leukocyte can be separated and extracted.

This is because when the whole blood is allowed to flow toward filter portion 114 including a gap having a size of 3 μm to 6 μm, the leukocyte is not easily deformed and remains in the place while the erythrocyte can be deformed easily and pass through the gap. It is not preferable that the gap provided in filter portion 114 is larger than 6 μm, because the leukocyte also passes through filter portion 114.

Use of filter device 100 of this exemplary embodiment makes it possible to extract only a specified substance from a solution containing substances. In particular, filter device 100 has filter portion 114 made of fibrous substance 115 with less variation in the diameter distribution, and thereby exhibits has a stable filtering effect in any positions in filter portion 114.

Even when filter portion 114 has a thickness of not more than 1 mm, it can have a small size and sufficient separation performance when fibrous substance 115 has the above-mentioned shape. When filter portion 114 has a thickness of larger than 1 mm, it is difficult to reduce the size.

When first port 112 is made to have a volume of at least about 2 $mm^3$, about 10 million cells of erythrocyte can be extracted from about 2 micro liters of whole blood.

Thus, by extracting only erythrocyte from the blood solution in this way, for example, Giemsa staining that targets only erythrocyte can be carried out rapidly and easily. This can suppress determination error by staining nucleic acid in leukocyte that is originally present in whole blood in staining. For example, mis-detection of nucleic acid in a malaria parasite can be suppressed. Thus, since highly accurate measurement using erythrocyte extracted with high accuracy can be carried out, it is possible to determine the presence or absence of onset of infectious diseases such as malaria infection from a stage in which no subjective symptoms are observed, which leads to the early detection of infectious diseases. Filter part 114 becomes able to remove aggregate platelet and leukocyte. Because platelet does not have a nucleic acid, it is not dyed, but may become the noise like a leukocyte by a pigment attaching to the surface of the platelet. In addition, it becomes easy to secure a field of view in case of the measurement and the detection cause of misplaced materials disappearing.

In addition, size and the state of the isolated erythrocyte become substantially uniform. This shows that unevenness depending on the measurement subject becomes small when the erythrocyte is measurement subject. Therefore, the measurement accuracy improves.

Conventionally when centrifugation is carried out for separating erythrocyte from the whole blood, an amount of the whole blood necessary for examination is large, or a number of treatment steps is increased for carrying out diluting the whole blood with a solvent to increase the volume and then carrying out centrifugation. However, when the filter device of the present disclosure is used, it is not necessary to use a large-scaled device such as a centrifugal separator and therefore it is not necessary to collect a large amount of sample blood. Therefore, by collecting about 1 micro liter of sample blood from, for example, the fingertip, and injecting it into first port 112, measurement can be carried out by using only erythrocyte and for a shorter time.

Furthermore, since the filter device of the present disclosure does not need a large-scaled and expensive device such as a centrifugal separator, it is suitable for a simple test at home, air ports and ports.

Note here that this exemplary embodiment describes a configuration in which filter portion 114 is formed throughout first flow passage 113, but filter portion 114 may be provided in at least a part of first flow passage 113. Furthermore, it is desirable that filter portion 114 is provided throughout at least not less than 500 micrometers from a connecting portion between first port 112 and first flow passage 113.

Figure 8:
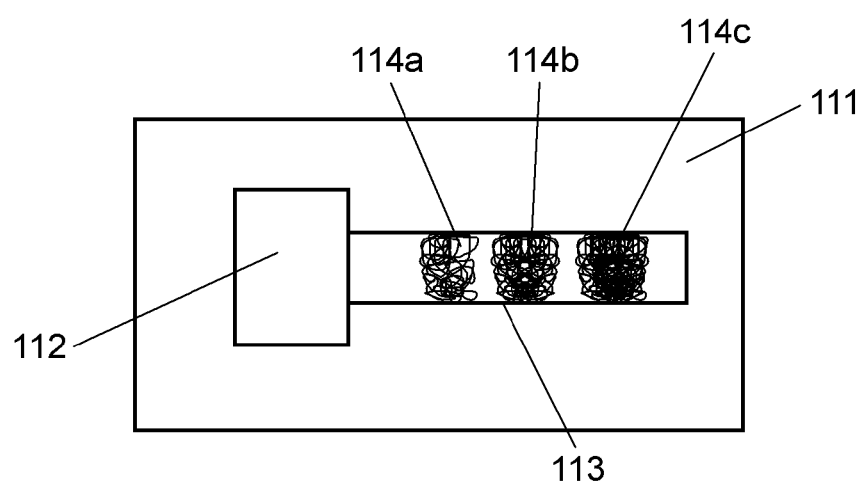
FIG. 8 is a top view of a filter device in accordance with the first exemplary embodiment.

FIG. 8 is a top view of the filter device in accordance with this exemplary embodiment. As shown in FIG. 8, filter device 100 may be provided with a multi-stage filter in which filter portions 114 (114a, 114b, and 114c) are formed in a plurality of places of first flow passage 113.

Furthermore, it is more preferable that filter portions 114 (114a, 114b, and 114c) formed in a plurality of places have only one peak in the diameter distribution of a plurality of fibrous substances constituting each filter portion 114, but that gaps made by a plurality of fibrous substances are different for each of filter portions 114 and become narrower toward the downstream of first flow passage 113. In other words, when filter portions 114 are gradually narrower toward the downstream of first flow passage 113 from filter portion 114a, filter portion 114b, and filter portion 114c sequentially in this order, filtering performance can be improved in stages while clogging is prevented.

Alternatively, gaps may be formed such that they become narrower toward the downstream in one filter portion 114. In this case, the same effect can be obtained. A larger substance is captured in the upstream of filter portion 114, so that the larger substance does not come to the downstream of filter portion 114. Thus, clogging does not easily occur.

This exemplary embodiment describes an example in which first flow passage 113 has flow passages on the substrate 111, but it is not necessary to form a flow passage on substrate 111. This exemplary embodiment can be carried out when first flow passage 113 has a capillary shape (cylindrical shape), and filter portion 114 is formed over the entire surface of the inner wall portion of first flow passage 113.

Figure 9:
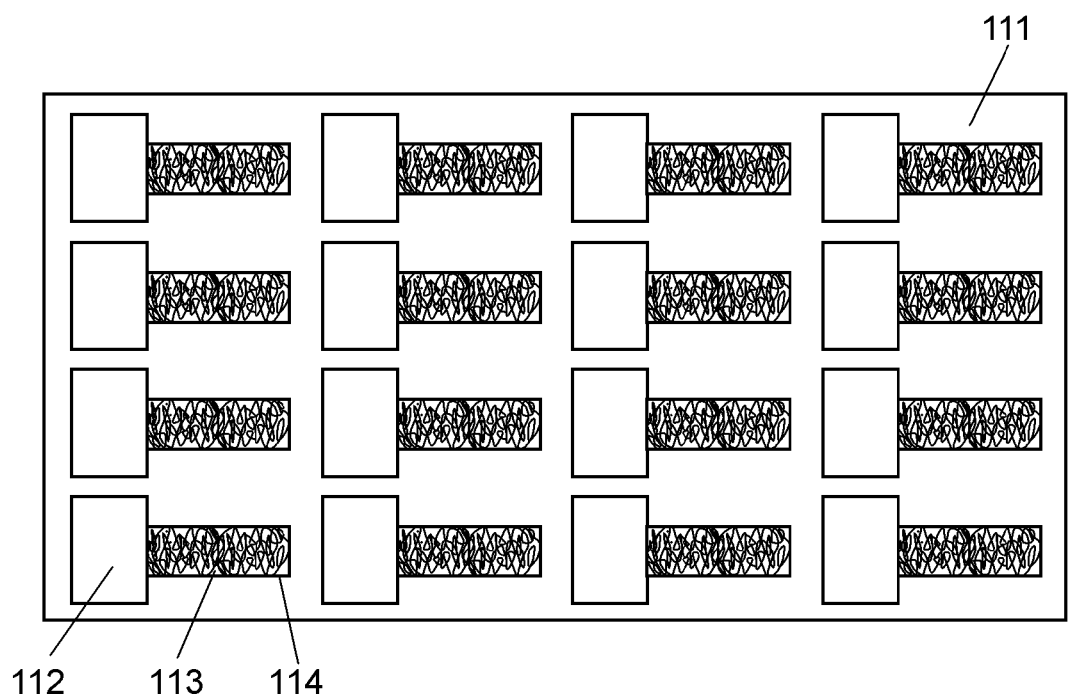
FIG. 9 is a top view of the filter device in accordance with the first exemplary embodiment.

FIG. 9 is a top view of a filter device in accordance with this exemplary embodiment. As shown in FIG. 9, filter devices 100 may be independently formed in an array on substrate 111. Each of filter devices 100 includes, on substrate 111, first port 112 and first flow passage 113 including filter portion 114. Thus, it is desirable that a plurality of the similar operations can be carried out at one time, and therefore an operation speed in extracting a specific substance can be improved. Furthermore, a plurality of measurement can be carried out at one time, which leads to shortening of the measurement time.

This exemplary embodiment describes a method of extracting erythrocyte from a blood solution, but filter device 100 of this exemplary embodiment is not limited to this example, and it may be used for extracting only a specimen as a specific material from a solution in a part of a micro reactor, a chemical chip, a biochip, a Lab-on-a-chip, a nanochip, or the like.

The living body materials included in erythrocyte is a target of the detection. In this case, the living body materials refer to organic matter such as the protein. After filtration, the living body materials are taken out by taking processing to hemolyze in erythrocyte. This method can be used for an infectious disease infecting erythrocyte including babesiasis and theileriosis not only malaria.

Second Exemplary Embodiment

Hereinafter, a filter device of this exemplary embodiment is described with reference to drawings. Note here that description for the portions described in the first exemplary embodiment is omitted. This exemplary embodiment is different from the first exemplary embodiment in that second port 217 for extracting a specific substance is provided.

Figure 10:
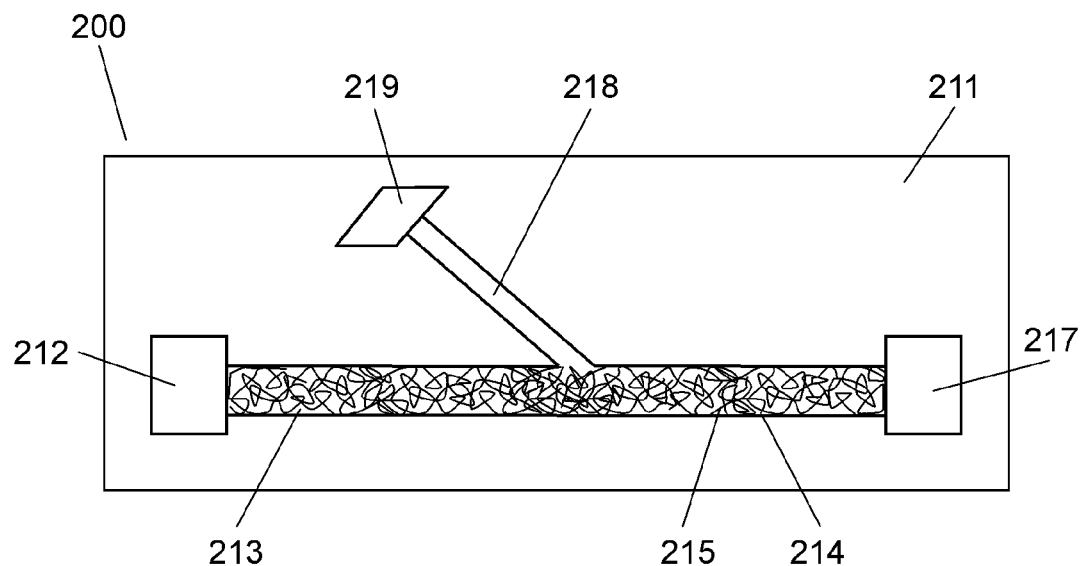
FIG. 10 is a top view of a filter device in accordance with a second exemplary embodiment of the present disclosure.

FIG. 10 is a top view of a filter device in accordance with this exemplary embodiment of the present disclosure. Filter device 200 of this exemplary embodiment includes second port 217. Second port 217 communicates with first flow passage 213 and extracts only a specimen from a solution. Furthermore, first flow passage 213 is provided with second flow passage 218. Second flow passage 218 is connected between first port 212 and second port 217. A buffer solution is allowed to flow from third port 219.

Second flow passage 218 can be provided by forming a flow channel on substrate 211 by fine processing such as an etching process. Substrate 211 can be formed of inorganic materials such as glass, silicon, thermal oxidation $SiO_2$, polysilicon, and amorphous silicon. Alternatively, substrate 211 can be also molded with resin such as PDMS, polypropylene, or polycarbonate, polyolefin, polystyrene, or the like.

Next, a method of extracting erythrocyte from a blood solution by using filter device 200 in this exemplary embodiment is described.

When blood as a sample is injected into first port 212, the injected blood gradually flows toward first flow passage 213. Herein, leukocyte is captured in a position near first port 212 of first flow passage 213. On the other hand, erythrocyte gradually permeates through first flow passage 213 and remains in first flow passage 213 in a state in which it is separated from leukocyte.

In order to extract erythrocyte from filter portion 214 made of fibrous substances 215 by avoiding a portion in which leukocyte is adsorbed, a buffer solution is allowed to flow from third port 219. The buffer solution flows into filter portion 214 of first flow passage 213 in which erythrocyte from second flow passage 218 remains, and erythrocyte together with the buffer solution starts to flow toward second port 217. Erythrocyte is taken out together with the buffer solution from second port 217, and then, it can be subjected to analysis of presence or absence, levels and types of infectious diseases by, for example, Giemsa staining by using other infectious disease test kits.

In this way, by extracting a specimen to the second port while a filtration product is allowed to remain in first flow passage 213, more efficient test or reaction can be carried out.

Instead of a method of extracting a specimen from second port 217 and testing it by using the other test kit, reaction can be carried out directly in second port 217. For example, in the case of testing of erythrocyte, a stain solution may be previously placed in second port 217. Furthermore, in the case of testing of protein, DNA, and the like, an antibody may be previously disposed in second port 217.

Note here that a method of observing reaction is not limited to observation under a fluorescence microscope. For example, a SAW (Surface Acoustic Wave) sensor provided with input/output electrodes is formed on both sides of second port 217 as a reaction field, and observation may be carried out by measuring a difference of frequencies between a case where a specimen is present in second port 217 and a case where the specimen is not present in second port 217.

Note here that it is desirable that second flow passage 218 is provided in such a manner that it is connected to a middle portion between first port 212 and second port 217 of first flow passage 213, or between the middle portion and second port 217.

This exemplary embodiment is described using third port 219 from which a buffer solution is allowed to flow, but third port 219 is not necessarily required. The buffer solution may be allowed to flow into second flow passage 218 directly.

Third Exemplary Embodiment

Hereinafter, a filter device of this exemplary embodiment is described with reference to drawings. Note here that description for the portion described in the first exemplary embodiment is omitted. This exemplary embodiment is different from the first exemplary embodiment in that a filter chip having through holes is formed in a capillary.

Figure 11:
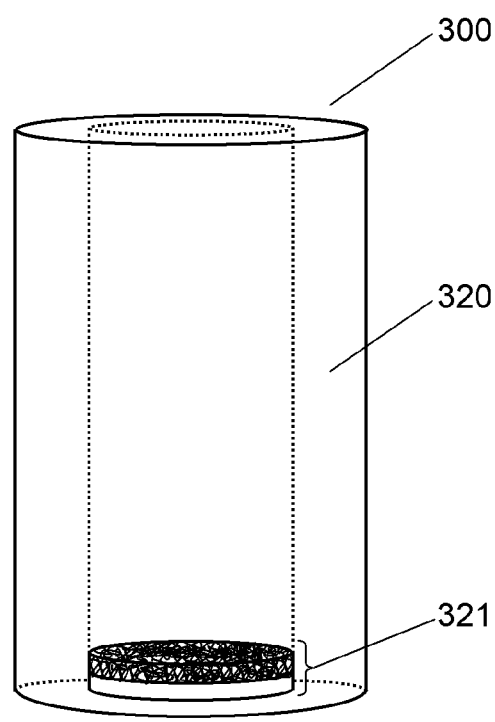
FIG. 11 is a perspective view of a filter device in accordance with a third exemplary embodiment of the present disclosure.
Figure 12:
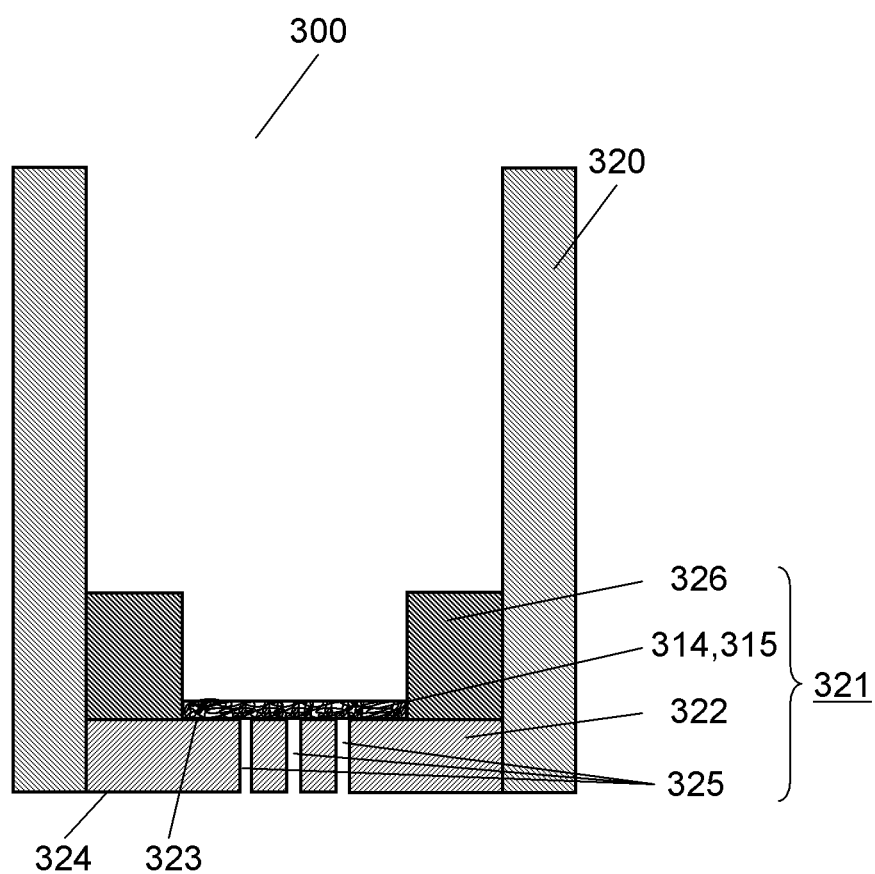
FIG. 12 is a sectional view of the filter device in accordance with the third exemplary embodiment.

FIG. 11 is a perspective view of a filter device in accordance with the third exemplary embodiment, and FIG. 12 is a sectional view thereof. As shown in FIG. 12, filter device 300 of this exemplary embodiment includes capillary 320 and filter chip 321. Filter chip 321 is provided at one end inside of capillary 320 such that a solution flowing in capillary 320 is brought into contact with filter chip 321. As shown in FIG. 12, filter chip 321 includes plate-like thin plate 322, and a plurality of through-holes 325. Through-holes 325 penetrate through first surface 323 and second surface 324 opposite to first surface 323 of thin plate 322. Filter portion 314 is provided so as to cover first surface 323 and portions above opening portions of plurality of through-holes 325 opened in first surfaces 323. Filter portion 314 is made of fibrous substances 315 including inorganic oxide.

A plurality of fibrous substances 315 are entangled with each other to form filter portion 314. Among solid substances contained in a solution, a substance whose maximum diameter is larger than a gap in fibrous substances 315 is captured as a filtration product by fibrous substance 315, and a substance whose maximum diameter is smaller than the gap in fibrous substances 315 passes through fibrous substances as a specimen. Thus, it is possible to separate a specimen and a filtration product in a solution. However, even a solid substance whose maximum diameter is larger than the gap in fibrous substances 315 can be extracted as a specimen if it can easily deform. Furthermore, the deformation ability can be employed when such a material passes through through-hole 325 provided below filter portion 314. Therefore, even when a specimen is larger than through-hole 325, it can pass through through-hole 325.

Fibrous substances 315 have one peak value in the diameter distribution, have small variation in diameters, and have no fibrous substances 315 having largely different diameters. Furthermore, when the diameter of fibrous substance 315 is substantially constant, an area of the gap is kept constant. Therefore, by controlling the diameter of fibrous substance 315, filter portion 314 has a stable filtering effect in any positions.

It is preferable that through-holes 325 are formed such that they are formed in parallel to the flow direction of a solution that flows in capillary 320, because occurrence of flow passage resistance can be suppressed.

Capillary 320 can be formed of inorganic materials such as glass, silicon, thermal oxidation $SiO_2$, polysilicon, and amorphous silicon. Alternatively, capillary 320 can be also formed of resin such as polydimethylsiloxane (PDMS), polypropylene, polycarbonate, polyolefin, polystyrene, polyamide, polymethylmethacrylate (PMMA), and cyclic polyolefin, and composite materials of such resin and glass. Alternatively, capillary 320 can be also molded from rubber, and a composite material of rubber and glass.

The size of the capillary are designed to be connected to the tip of general-purpose container including a living body sample (e.g., syringes). The shape of the capillary may have a taper shape to fit in the tip of the container. By this constitution, liquid leak can be minimized.

In this exemplary embodiment, filter chip 321 is provided at one end of capillary 320, but it needs to be arbitrarily formed so that it is brought into contact with a solution flowing in capillary 320. It is more preferable that filter chip 321 is provided such that through-holes 325 are parallel to the flow direction of the solution that flows in capillary 320 and that thin plate 322 is formed in a direction with an arbitrary angle with respect to the flow direction of the solution flowing in capillary 320.

The arbitrary angle is desirably being orthogonal. However, thin plate 322 is required to be configured so that the solution certainly passes between fibrous substances 315 and inside through-hole 325 when the solution flowing in capillary 320 moves from first surface 323 toward second surface 324 of thin plate 322.

The solution flow direction means a flow direction of a fluid as an average. In particular, as shown in FIG. 12, when the wall surfaces of capillary 320 are parallel to each other and when the width of flow passage of capillary 320 is constant, the solution flow direction means a direction parallel to the wall surface. On the other hand, when the wall surfaces of capillary 320 are not parallel to each other and when the width of flow passage of capillary 320 is not constant, that is, when the width is gradually narrower along the solution flow direction (not shown) or when the width is gradually wider along the solution flow direction (not shown), the solution flow direction shows the flow direction of a fluid as an average. The flow direction can be parallel to the axis of the capillary 320.

Figure 13:
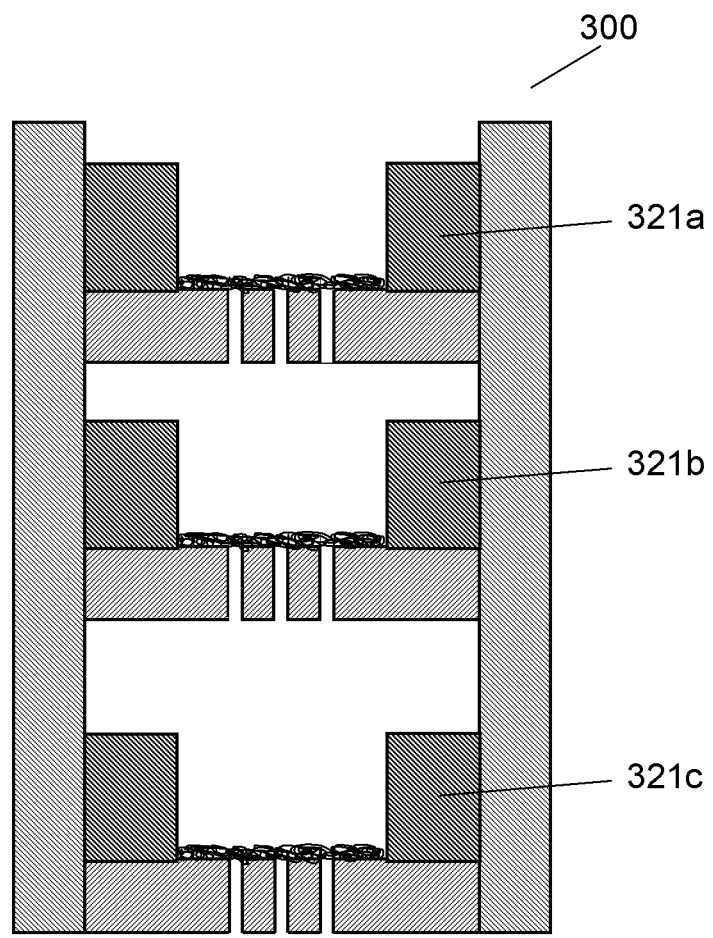
FIG. 13 is a sectional view of the filter device in accordance with the third exemplary embodiment.

In this exemplary embodiment, filter chip 321 is provided at one end of capillary 320 and the number of filter chip 321 is one, but a plurality of filter chips 321 (321a, 321b, and 321c) may be provided inside capillary 320 as shown in FIG. 13.

Furthermore, in the plurality of filter chips 321 (321a, 321b, and 321c), gaps made by a plurality of fibrous substances 315 constituting filter portion 314 are different for each filter chips 321. It is more preferable that the gaps are narrower toward the downstream of capillary 320. That is to say, the size of filter chips 321 becomes gradually narrower toward the downstream of capillary 320 from filter chip 321a, filter chip 321b, and filter chip 321c sequentially in this order, and thereby filtering performance can be improved in stages. Alternatively, the gaps may be formed such that they become narrower toward the downstream in one filter portion 314. In this case, the same effect can be exhibited. With such a configuration, since a large substance is firstly captured in the upstream of filter portion 314, and a large substance does not come to the downstream of filter portion 314, clogging by the filtered substance can be prevented.

Furthermore, as long as filter chip 321 is joined without leakage to capillary 320 in the portion other than through-holes 325, filter chip 321 may be joined to capillary 320 directly or joined via an adhesive layer.

Figure 27:
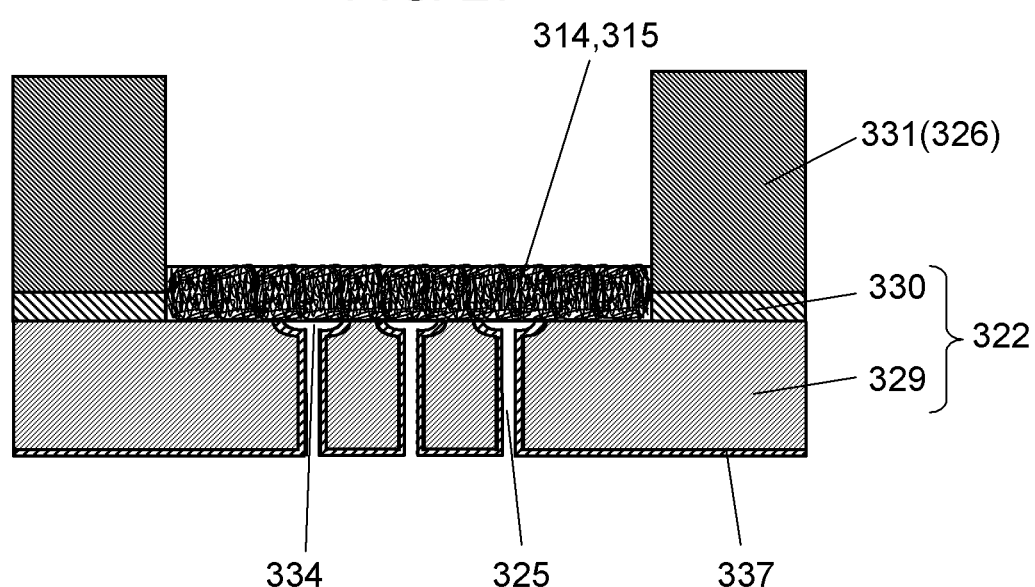
FIG. 27 is a sectional view showing a manufacturing step of the filter device in accordance with the third exemplary embodiment.

It is desirable that an SOI (Silicon on Insulator) substrate whose silicon layer includes silicon (100) is used as a base material for producing filter chip 321. The SOI substrate has a three-layered structure of a silicon layer—a silicon dioxide layer—a silicon layer. When the SOI substrate is used, as shown in FIG. 27, it is possible to form thin plate 322 made of silicon layer 329 on the surface of which silicon dioxide layer 330 is formed.

Further, by using an SOI substrate, the SOI substrate can be subjected to fine processing by using photolithography and etching technique, and thereby a large number of precise sensor chips 321 can be produced at one time. When the SOI substrate is subjected to an etching process, since silicon dioxide layer 330 functions as an etching stop layer, highly precise fine chips 321 can be produced. Furthermore, since silicon dioxide layer 330 is hydrophilic, generation of air bubbles at the time of measurement can be suppressed and air bubbles can be removed easily. As a result, highly precise measurement can be carried out.

It is preferable that the thickness of silicon dioxide layer 330 is 0.5 to 10 μm from the viewpoint of the thickness required for the etching stop layer and productivity.

It is preferable that filter chip 321 is provided with holding portion 326 for holding thin plate 322 from the viewpoint of the handling and the mounting property in manufacturing process since the thickness of holding plate 322 having a plurality of through-holes 325 may be several μm. When the SOI substrate is used, holding portion 326 can be formed of silicon layer 331.

Figure 14:
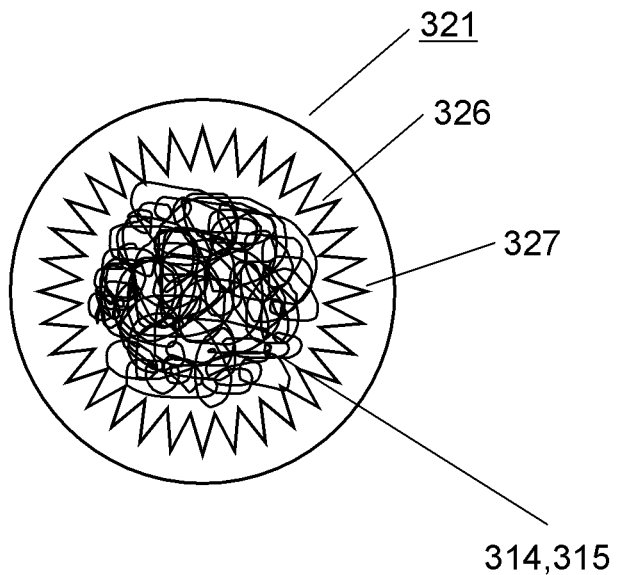
FIG. 14 is an enlarged top view of a part of the filter device in accordance with the third exemplary embodiment.
Figure 15:
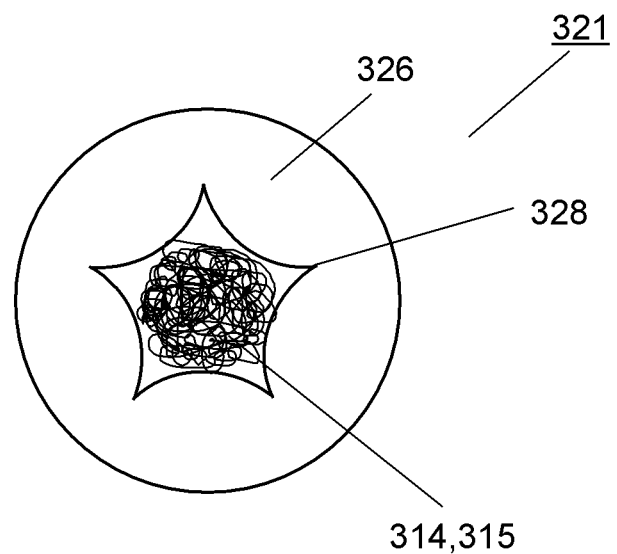
FIG. 15 is an enlarged top view of a part of the filter device in accordance with the third exemplary embodiment.

When holding portion 326 is provided, it is desirable that at least one or more of protruding portions 327 are provided on the inner wall of holding portion 326 as shown in a top view of filter chip 321 in FIG. 14. Alternatively, as shown in a top view of filter chip 321 in FIG. 15, it is desirable that at least one acute-angled recess portion 328 is provided on the inner wall of holding portion 326. By providing protruding portion 327 or acute-angled recess portion 328 is provided on the inner wall of holding portion 326, when a solution is introduced into holding portion 326, air bubbles in a solution tend to flow along protruding portion 327 or acute-angled recess portion 328, thereby making it difficult for air bubbles to remain in filter chip 321. In this way, since air bubbles can be suppressed, the filtering accuracy can be improved.

Formation of holding portion 326 includes a method of etching the SOI substrate, sticking, and the like. Etching from the SOI substrate is preferable from the viewpoint of the consistency of process. For example, when silicon layer 331 of the SOI substrate is used as holding portion 326 of filter chip 321, it can play a role of maintaining mechanical strength and a role of storing liquid. Holding portion 326 is not an indispensable component, but may be optionally employed as a component of filer chip 321 depending on the shape and structure of filter chip 321.

The thickness of thin plate 322 is desirably about 5 μm to 100 μm. Thin plate 322 that is easily structurally weak does not easily crack when the thickness of thin plate 322 is increased, but time necessary for processing is increased. Therefore, the thickness of thin plate 322 is desirably thin from the viewpoint of the throughput of steps. Furthermore, when the thickness of thin plate 322 is increased, the length of through-hole 325 is increased. Consequently, specimens do not easily pass, and the yield of specimens that are desired to be collected after they pass through filter chip 321 is lowered.

In the above examples, an SOI substrate whose silicon layer 329 is silicon (100) is selected as a base material for producing filter chip 321. However, it is also possible to use other substrates including a silicon (110) substrate, a silicon (111) substrate, silicon substrates with other orientations, a glass substrate, film resin, or the like.

More preferably, as a base material for producing filter chip 321, it is desirable to use a laminated structure of two or more materials, for example, silicon and silicon dioxide, having a large difference in etching rates.

From the viewpoint of workability and versatility, it is preferable to use a substrate including silicon (100). The substrate including silicon (100) may be a substrate including at least silicon (100), and does not necessarily mean a substrate consisting only of silicon (100). An SOI substrate whose silicon layer uses silicon (100), a substrate partially or entirely doped with elements such as boron, or a substrate formed by sticking silicon (100) onto glass or the like, may be used.

The silicon dioxide layer that functions as an etching stop layer is generally a silicon dioxide layer formed by thermal oxidation. The silicon dioxide layer can be formed by other methods such as a CVD (Chemical Vapor Deposition) method, a sputtering method, a CSD (Chemical Solution Deposition) method, or the like. Furthermore, the silicon dioxide layer may be doped-oxide layers such as a so-called PSG (Phosphorus Silicon Glass) layer doped with phosphorus, a so-called BSG (Boron Silicon Glass) layer doped with boron, or a BPSG (Boron Phosphorus Silicon Glass) layer doped with phosphorous and boron. Furthermore, not only a layer including silicon dioxide as a main component mentioned above but also an inorganic oxide layer or an inorganic nitride layer such as silicon nitride, silicon oxynitride, and aluminum oxide, which have a difference in etching rates with respect to silicon, can be used.

It is desirable that a plurality of through-holes 325 are provided. The number of through-holes 325 is not limited. Any number of through-holes can be formed by changing the number of mask holes in a resist mask in a photo-etching process.

Increasing of the number of through-holes 325 is preferable because the workability of the filter is improved. For example, when the number of through-holes 325 is increased, since specimens can easily pass, the same amount of test materials can be allowed to pass through a filter for a short time without increasing the amount of specimens or filtering time.

The diameter of through-hole 325 is appropriately adjusted to a value suitable for suppressing the generation of the flow passage resistance of a solution.

For example, when filter device 300 is used for filtering a blood solution and extracting erythrocyte as a subject specimen, the diameter of through-hole 325 is desirably not less than 3 μm. Although the size of erythrocyte is 7 μm to 8 μm in diameter, erythrocyte can enter and pass through a narrow capillary blood vessel whose diameter is not larger than half of the diameter of erythrocyte itself. However, when through-hole 325 is than 3 μm or less, the passing efficiency of erythrocyte may be lowered.

The shape of through-hole 325 can be also changed by changing the shape of the mask holes when the resist mask is formed. The shape of through-hole 325 is not particularly limited and optimal shapes can be selected depending upon the types and shapes of specimens to be measured.

Furthermore, it is desirable that the shapes of the opening portions of the plurality of through-holes 325 in first surfaces 323 of thin plate 322 are formed in a honeycomb shape. Thus, without damaging the strength of thin plate 322, a larger number of through-holes 325 per unit area can be formed.

In the alternative, it is preferable that the shapes of the opening portions of through-holes 325 in first surface 323 of thin plate 322 are formed in a circular shape. When the shapes of the opening portions of through-holes 325 have a circular shape, when specimens pass through through-hole 325, they can pass through through-hole 325 smoothly without being captured by through-hole 325. For example, when erythrocyte is extracted as a specimen, even if the erythrocyte have less flexibility or elasticity depending upon the states, the erythrocyte can be isotropically sucked from a part below second surface 324, when the shapes of the opening portions of through-holes 325 are circular. Therefore, it is possible to suppress the generation of a force in a specific direction of the specimen. As a result, damage to the specimen is small, and the specimen can easily pass through through-hole 325.

In order to increase the density of through-holes 325 in filter chip 321, it is also possible to make the shapes of opening portions of the plurality of through-holes 325 a regular polygon.

When a plurality of through-holes 325 are formed, a length between centers of most adjacent through-holes 325 may be selected based on the longest dimension of specimen according to shapes of specimens. For example, when filter device 300 is used by targeting erythrocyte as a specimen by using blood, it is desirable that the interval between through-holes 325 is not smaller than 10 μm from the success rate of extraction, because in general, the size of erythrocyte is not less than 10 μm. When the interval of through-holes 325 is not larger than 10 μm, interference between erythrocytes occurs, and therefore the success rate of extraction is reduced. When a cell is used as a specimen, depending upon the types or culture conditions of specimens, the size of the cell is generally about 20 μm. Therefore, the interval of through-holes 325 is desirably not less than 20 μm.

On the other hand, by increasing the distance between through-holes 325, structurally weak portions are not easily closely gathered. Therefore, the reliability of filter chip 321 is improved.

However, when the interval between through-holes 325 is set to be large, in order to improve the filtering speed or the extraction rate of specimens, a large number of holes are necessary. Therefore, a region necessary for forming through-holes 325 increases, which makes it difficult to make a sensor smaller or to reduce the cost. In this exemplary embodiment, the interval between through-holes 325 is set to 50 μm in order to prevent specimens from interfering with each other by setting the interval between through-holes 325 sufficiently large.

Regarding thin plate 322, when a material such as a silicon single crystal that is weak in a specific direction is used, if through-holes 325 are aligned in the specific weak direction, the structure may become weak. Therefore, it is desirable that through-holes 325 are arranged in such a manner that the most adjacent through-holes 325 are not aligned in the specific weak direction. Herein, the specific weak direction is referred to as a cleavage plane for a silicon single crystal. Thus, through-holes 325 need to be arranged in such a manner that they are not along the cleavage plane. The structural strength can be maintained as long as through-holes 325 are arranged in such a manner that line segments connecting the centers of the most adjacent through-holes 325 are not along the cleavage plane.

The intervals between through-holes 325 are preferably equal, and they are desirably bilaterally symmetry to each other. More desirably, it is desirable that through-holes 325 are arranged with point symmetry to each other in the middle point of thin plate 322. To do so, for example, when suction is carried out from one end of capillary 320, symmetry occurs in a suction pressure, specimens pass through through-hole 325 uniformly. Accordingly, specimens are not closely gathered in a specific place, and therefore, clogging does not occur in filter portion 314. Thus, the reliability of filter chip 321 is improved.

It is desirable that fibrous substance 315 is directly jointed to thin plate 322. Herein, "directly joined" means that fibrous substance 315 is directly formed on thin plate 322, and atoms or molecules constituting thin plate 322 and fibrous substance 315 are directly connected to each other. It generally means a state in which the molecules are covalently bonded to each other. For example, when silicon is used on the surface of thin plate 322, fibrous substance 315 is formed by using the silicon as a raw material. Thus, silicon atoms of thin plate 322 and silicon atoms in fibrous substance 315 are covalently bonded via oxygen molecules in the atmosphere of formation of fibrous substance 315, and direct joining can be achieved.

Since fibrous substances 315 are entangled with each other, and have a plurality of branches, filter portion 314 is firmly formed with respect to first surface 323 of thin plate 322. Furthermore, when fibrous substances 315 are bent respectively and entangled with each other, filter portion 314 is formed such that spaces from various directions including portions above the opening portions of through-holes 325 in first surface 323 of thin plate 322 are easily covered.

A gap formed between fibrous substances 315 is required to have its shortest distance to be smaller than the size of a filtration product.

For example, when a blood solution is used as a solution and filter device 300 is used so as to extract erythrocyte as a subject specimen, filter portion 314 desirably has a gap having a size of 3 μm to 6 μm. The size of erythrocyte is 7 μm to 8 μm in diameter, and can enter a capillary blood vessel having a diameter that is not more than the half of the diameter of erythrocyte itself. The leukocyte has a spherical shape having a size of 6 μm to 30 μm, and the smaller deformation ability than that of flat erythrocyte. In a region in which a gap of filter portion 314 is 3 μm to 6 μm, only erythrocyte can be allowed to pass. It is not preferable that the size of a gap is larger than 6 μm because leukocyte also passes filter portion 314.

Figure 16:
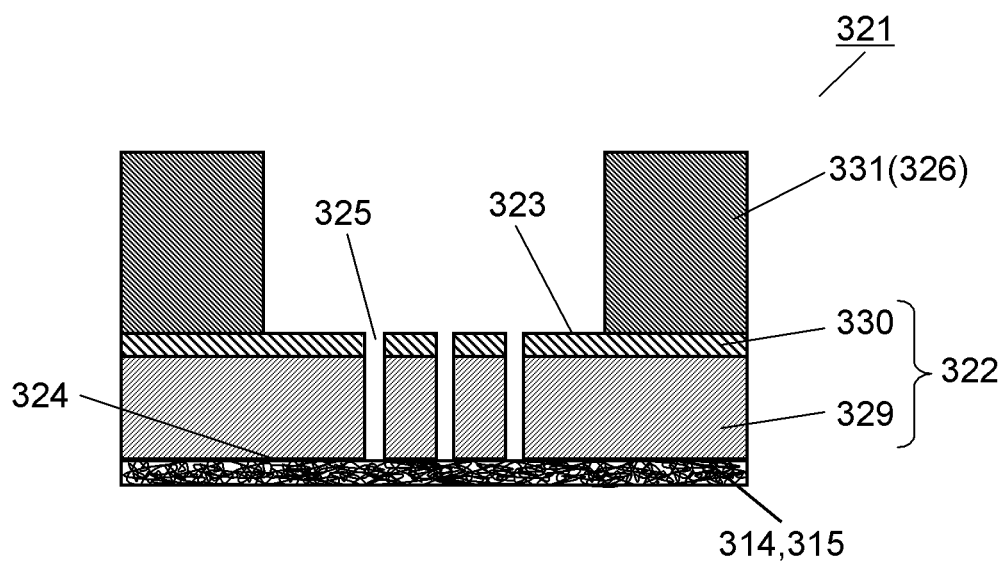
FIG. 16 is an enlarged sectional view of a part of the filter device in accordance with the third exemplary embodiment.

In this exemplary embodiment, fibrous substance 315 is formed so as to cover first surface 323 and portions above the opening portions of plurality of through-holes 325 opened in first surfaces 323. However, as shown in FIG. 16, fibrous substance 315 may be provided on at least one side of first surface 323 and second surface 324. The same effect can be obtained when fibrous substance 315 is formed only on second surface 324. In such a case, it is preferable that first surface 323 includes silicon dioxide layer 330 to make the surface hydrophilic.

Figure 17:
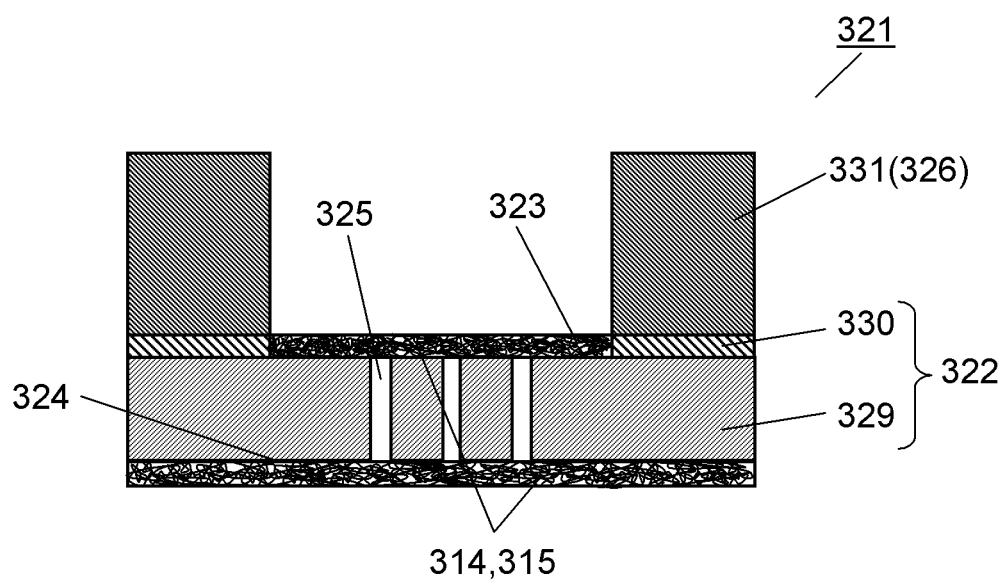
FIG. 17 is an enlarged sectional view of a part of the filter device in accordance with the third exemplary embodiment.

Furthermore, as shown in FIG. 17, fibrous substance 315 may be provided on both surfaces of first surface 323 and second surface 324.

Figure 18:
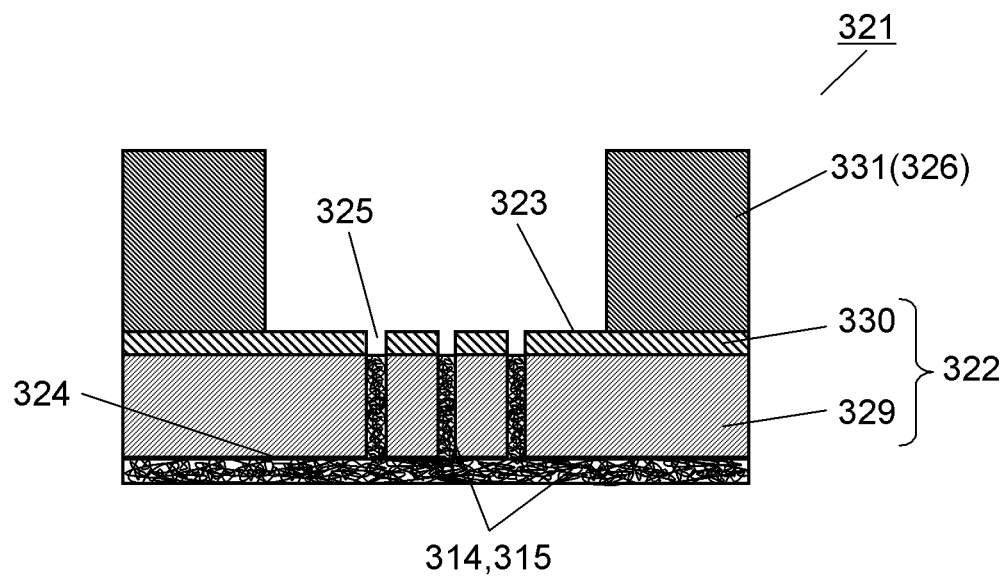
FIG. 18 is an enlarged sectional view of a part of the filter device in accordance with the third exemplary embodiment.

Furthermore, as shown in FIG. 18, fibrous substance 315 may be provided inside through-holes 325. Alternatively, fibrous substance 315 may be provided in first surface 323 and/or second surface 324, and inside through-holes 325. When fibrous substance 315 is not formed on first surface 323, first surface 323 is required to be subjected to treatment for making the surface hydrophilic, and is preferably formed of silicon dioxide layer 330.

Figure 19:
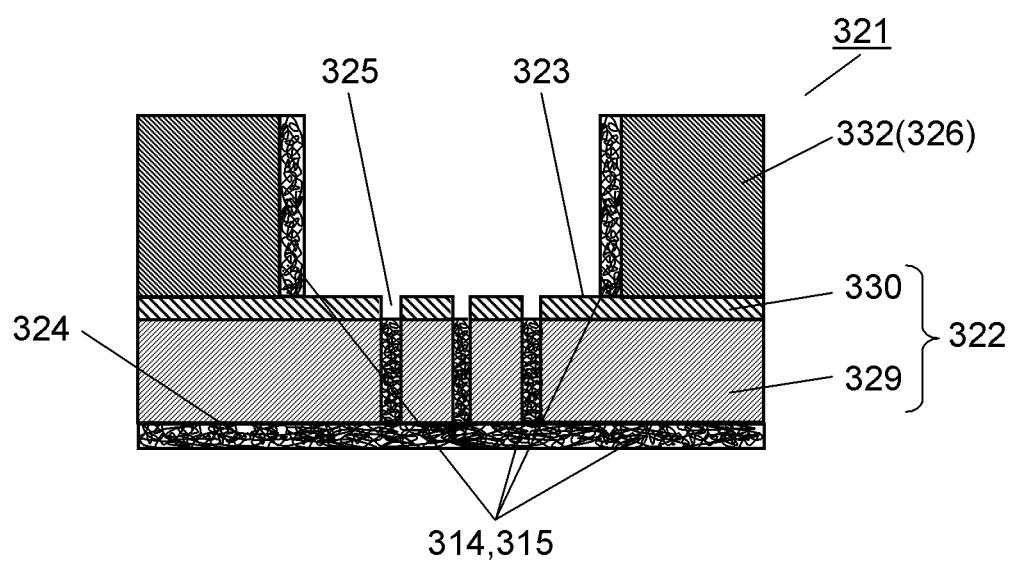
FIG. 19 is an enlarged sectional view of a part of the filter device in accordance with the third exemplary embodiment.

Furthermore, as shown in FIG. 19, fibrous substance 315 may be further provided on the surface of holding portion 326.

Any of the above-mentioned cases have the same or similar effects as in this exemplary embodiment.

Next, regarding a method of manufacturing filter device 300, firstly, a method of manufacturing filter chip 321 is described.

Herein, a method of manufacturing filter chip 321 including filter portion 314 made of fibrous substances 315 on first surface 323 of thin plate 322 is described.

FIGS. 20 to 27 are sectional views each showing a step of manufacturing of the filter device in this exemplary embodiment.

Figure 20:
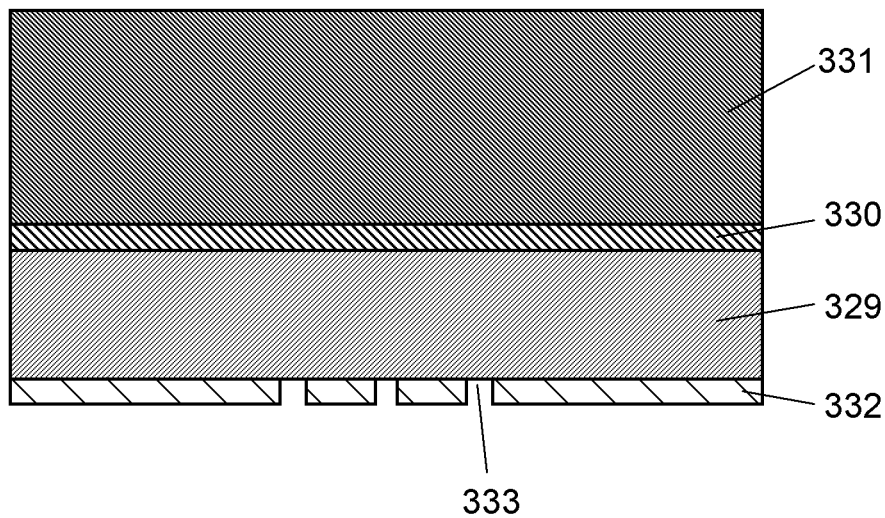
FIG. 20 is a sectional view showing a manufacturing step of the filter device in accordance with the third exemplary embodiment.

Firstly, as shown in FIG. 20, as a base material for producing filter chip 321, an SOI substrate having a three-layered structure of silicon layer—silicon dioxide layer—silicon layer in which silicon layer 329 includes a silicon (100) plane is prepared.

Then, first resist mask 332 is formed on the surface of silicon layer 329 (a lower surface in FIG. 20). At this time, a plurality of sensor chips 321 can be simultaneously formed in one substrate by using a plurality of mask holes 333 having substantially the same shapes as those on the cross-sectional surface of desired through-holes 325.

Figure 21:
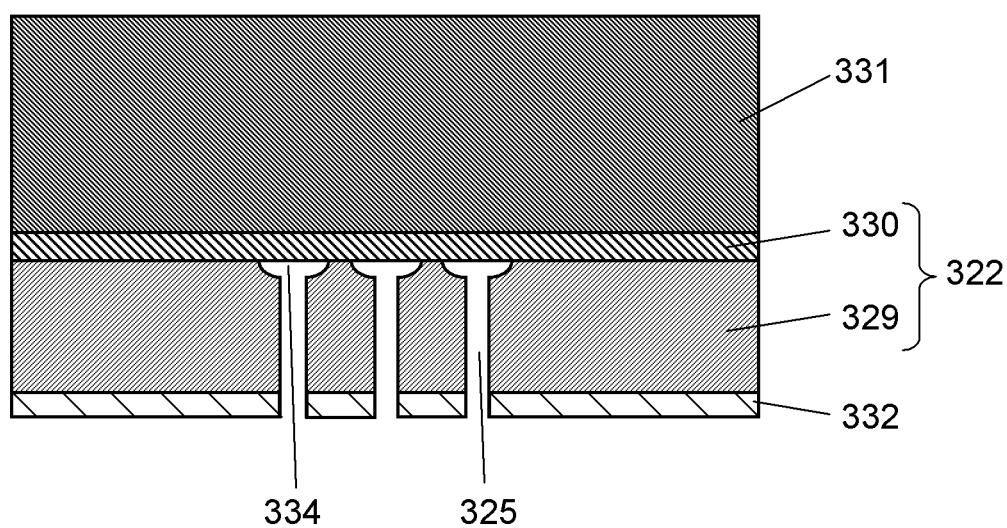
FIG. 21 is a sectional view showing a manufacturing step of the filter device in accordance with the third exemplary embodiment.

Next, as shown in FIG. 21, silicon layer 329 is etched from the mask holes 333 side so as to form through-hole 325. An etching process at this time is desirably dry etching because fine processing can be carried out at high accuracy. When dry etching is carried out, in order to form through-holes 325 having a high aspect ratio, that is, being deep with respect to the hole diameter, gas for promoting etching (etching gas) and gas for suppressing etching (suppressing gas) are alternately used. In this exemplary embodiment, $SF_6$ is used as the etching gas, and $C_4F_8$ is used as the suppressing gas. In a dry etching step, plasma is generated by an inductive coupling method of an external coil, and $SF_6$ as an etching gas is introduced therein. Then, F radicals are generated. Then, the generated F radicals are reacted with silicon layer 329 and silicon layer 329 is chemically etched.

At this time, when high frequency is applied to silicon layer 329, a negative bias voltage is generated in silicon layer 329. Then, positive ions ($SF_5^+$) contained in the etching gas vertically collides with silicon layer 329, and silicon layer 329 is physically etched by the ion bombardment. In this way, dry etching proceeds vertically inside silicon layer 329.

On the other hand, when suppressing gas $C_4F_8$ is used, high frequency is not applied to silicon layer 329. Thus, no bias voltage is generated in silicon layer 329. Therefore, $CF^+$ contained in the suppressing gas $C_4F_8$ is attached onto the wall surface of the dry-etched holes of silicon layer 329 without being deflected, and a uniform polymerized film (not shown) made of fluorocarbon is formed on the surface thereof.

This fluorocarbon film works as a polymerized film and suppresses etching. This polymerized film is formed not only on the wall surface portion but also on the bottom surface of through-hole 325. Since the polymerized film formed on the bottom surface of through-hole 325 is more easily removed by ion bombardment as compared with the polymerized film formed on the wall surface, etching proceeds in the vertical direction. When such etching is carried out repeatedly, the etching then reaches the surface of silicon dioxide layer 330, and the processing of etching in the deep direction stops at an expressed surface of silicon dioxide layer 330.

As shown in FIG. 21, it is possible to provide concave portion 334 in the vicinity of the boundary between silicon layer 329 and silicon dioxide layer 330 inside through-holes 325. Silicon dioxide layer 330 has a property that it is not easily etched in the above-mentioned etching conditions. Thus, etching proceeds, and reaches the surface of silicon dioxide layer 330, the proceeding of the etching in the depth direction stops at the expressed surface of silicon dioxide layer 330.

Thereafter, etching is further carried out, etching ions are accumulated on the expressed surface of silicon dioxide layer 330, and etching ions and the etching ions accumulated on the surface of silicon dioxide layer 330 repel each other, and the etching ions start to proceed in the lateral (horizontal) direction. Therefore, in the vicinity of silicon dioxide layer 330, concave portion 334 in which the opening width is gradually increased in a taper shape can be formed.

In this way, when thin plate 322 is formed in a laminated structure of silicon layer 329 as a conductive material and silicon dioxide layer 330 as an insulating material, etching easily proceeds in the lateral direction (horizontal direction) on the surface of silicon dioxide layer 330, and concave portion 334 can be formed.

The depth of concave portion 334 is about 1 μm. The depth can be controlled depending upon the etching time.

As the etching gas, $CF_4$ can be used in addition to $SF_6$. As a suppressing gas, for example, $CHF_3$ can be used in addition to $C_4F_8$.

Note here that according to the etching method, in general, silicon is etched substantially vertically, but depending upon the etching conditions, tapering can be controlled. Herein, for example, by increasing an amount of suppressing gas, it is desirable to form sequential tapering that broadens in the etching direction by employing conditions in which suppressing of etching is strong. Thus, a flow passage resistance is reduced, and flow becomes smooth.

The opening portion of through-hole 325 in holding plate 322 may be provided with a recess shape (not shown). When a recess shape is provided at the first surface side of holding plate 322 that holds filtration products, specimens or filtration products are easily closely gathered in the vicinity of through-hole 325, and therefore the extraction efficiency of specimens and the success rate of measurement are improved.

Furthermore, when a recess shape is formed at second surface 324 side of through-hole 325 in thin plate 322 in which filter portion 314 made of fibrous substances 315 is not formed, the flow passage resistance can be suppressed. Therefore, clogging does not easily occur in filter portion 314, and therefore working efficiency of filter is improved. As a result, the yield of specimens is improved.

For formation of the above-mentioned recess, from the viewpoint of the mass production, it is preferable to employ wet etching with an alkaline solution. In this case, since the etching speed is generally satisfies the relation: silicon (100) plane>silicon (110) plane>>silicon (111), a pyramid-shaped recess shape is formed.

Furthermore, for formation of the recess shape, gas etching capable of etching silicon, for example, $SF_6$, $CF_4$, $Cl_2$, and $XeF_2$, can be used. According to this method, shapes of the recesses can be controlled variously.

First resist mask 332 may be removed at this point, but it is more preferable that it is removed at the same time when second resist mask 335 is removed because efficiency is enhanced.

Figure 22:
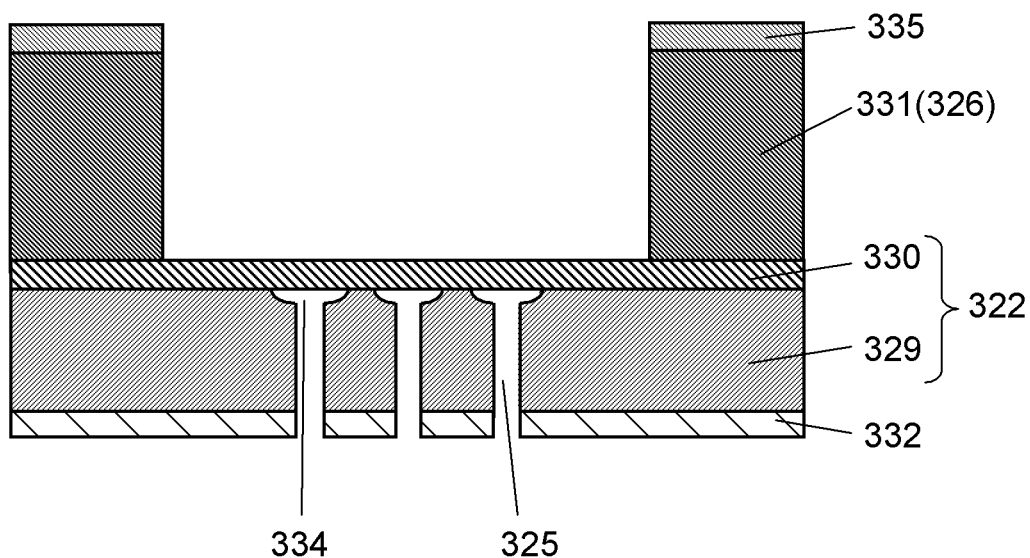
FIG. 22 is a sectional view showing a manufacturing step of the filter device in accordance with the third exemplary embodiment.

Next, as shown in FIG. 22, second resist mask 335 is formed on the surface (an upper surface in FIG. 22) of silicon layer 331. Thereafter, silicon layer 331 is etched in the etching conditions when silicon layer 329 is etched so as to form holding portion 326.

The proceeding of the etching in the depth direction also stops at an expressed surface of silicon dioxide layer 330.

At this time, in particular, since cycles of etching and deposition are repeated so as to carry out etching, the inner wall surface of holding portion 326 may be in a scallop shape (not shown) on which concavity and convexity are formed. A stepped shape generated on the inner wall of through-hole 325 is called scallop. The step of the scallop is in the order of several nm to several tens nm. It is possible to find whether or not this etching is used by observing a "scallop shape."

Figure 23:
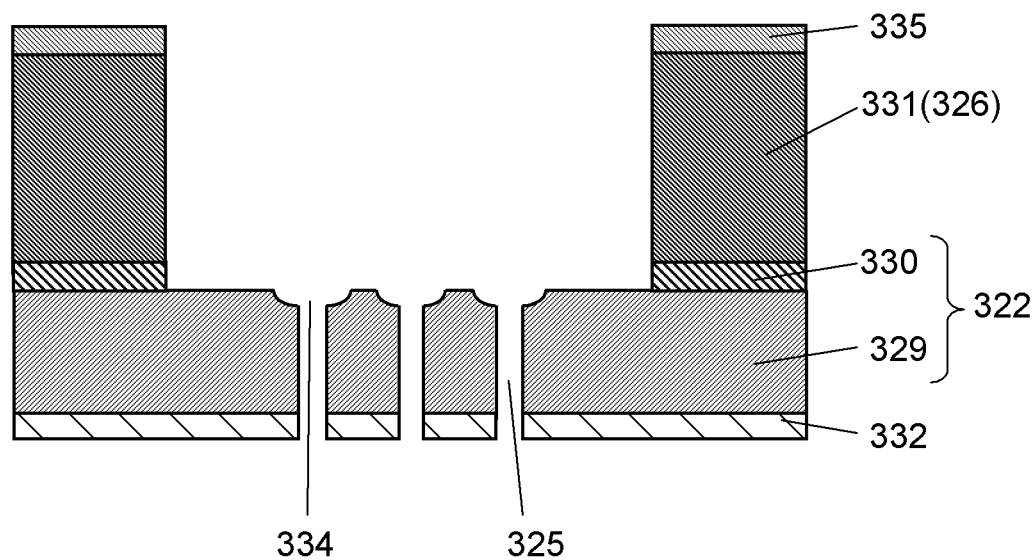
FIG. 23 is a sectional view showing a manufacturing step of the filter device in accordance with the third exemplary embodiment.

Next, as shown in FIG. 23, silicon dioxide layer 330 is dry-etched from the upper surface side. As the etching gas used for dry etching, for example, a mixed gas of $CHF_3$ and Ar is used. The mixed gas of $CHF_3$ and Ar is an etching gas having high straightness by Ar gas excited with plasma. When a large amount of the etching component, for example, an Ar gas, for carrying out sputtering, is used, etching straightly advances and enters from the inside of holding portion 326, and only silicon dioxide layer 330 as an insulating material can be etched. Furthermore, $CHF_3$ does not easily form a polymerized film on the surface of silicon dioxide layer 330, but forms a polymerized film made of fluorocarbon on the surface of silicon layer 331. Etching does not proceeds easily on the surface of silicon layer 331 due to the polymerized film formed on the surface of silicon layer 331, only silicon dioxide layer 330 is easily etched.

Other examples of the etching gas used at this time include $CF_4/H_2$, $CHF_3/SF_6/He$, or the like, in addition to a mixed gas of $CHF_3$ and Ar.

As described above, when thin plate 322 is formed of two kinds of materials, that is, silicon layers 329 and 331 and silicon dioxide layer 330 in a laminated body, the two types of materials have different etching rates with respect to the same gas, respectively. Therefore, when silicon layers 329 and 331 are etched, silicon dioxide layer 330 is not etched. On the contrary, when silicon dioxide layer 330 is etched, silicon layers 329 and 331 are not etched. Etching is carried out by using such a property, and thereby a desired shape of through-hole 325 can be easily formed.

Note here that for etching of silicon dioxide layer 330, wet etching using HF, BHF, $NH_4F$, and the like, may be carried out.

Then, filter portion 314 made of fibrous substances 315 is provided so as to cover first surface 323 of filter chip 321 and portions above the opening portions of plurality of through-holes 325 opened in first surfaces 323.

Examples of a method of forming fibrous substance 315 include a method of forming fibrous substance 315 from a portion provided with catalyst layer 336 by using catalyst layer 336.

Figure 24:
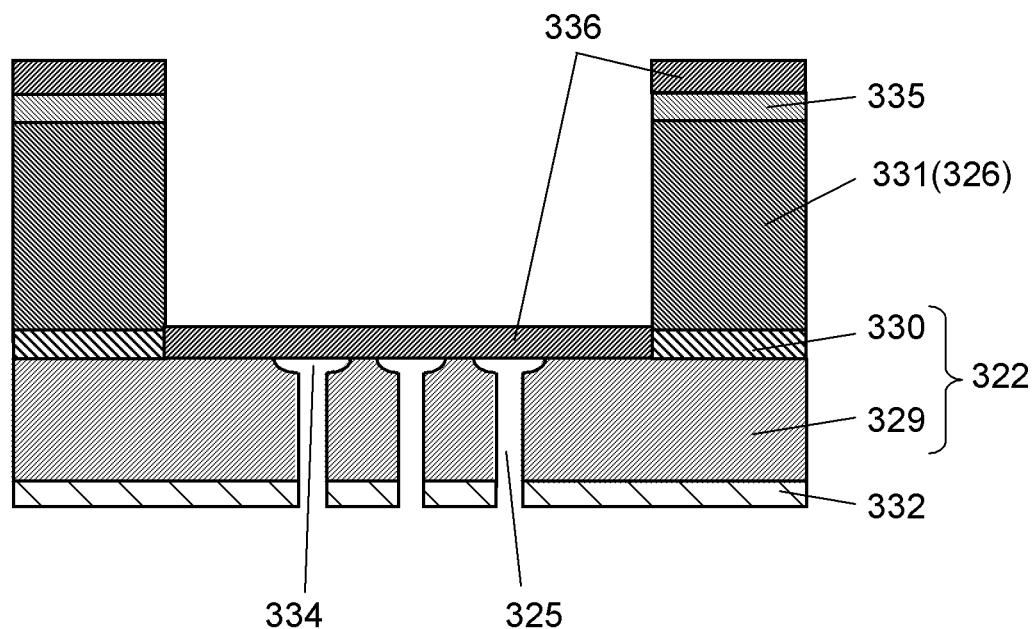
FIG. 24 is a sectional view showing a manufacturing step of the filter device in accordance with the third exemplary embodiment.

As shown in FIG. 24, catalyst layer 336 is formed from first surface side of silicon layer 329, that is, the upper surface of through-hole 325 (an upper surface of FIG. 24). At this time, in a region in which second resist mask 335 is formed, catalyst layer 336 is formed on the upper surface of second resist mask 335. The thickness of catalyst layer 336 is generally not more than 100 nm.

As catalyst layer 336, for example, metals such as Fe, Co, Ni or Au can be used other than Pt, and types of metals are not particularly limited.

Note here that as a method of forming catalyst layer 336, any methods such as a CVD method, a sputtering method, a CSD method, an ALD (Atomic Layer Deposition) method can be employed. Furthermore, catalyst layer 336 may be present in a state in which it is dispersed in the other materials such as organic substances.

Instead of forming catalyst layer 336, catalyst layer 336 may be previously implanted in the surface on which fibrous substance 315 of silicon layer 329 is to be formed. At this time, a catalytic material is present in a form in which it is contained in silicon layer 329. For this, an ion implantation method is suitably used. The ion implantation method is a method of electrically accelerating ions and allowing ions to collide with an object, thereby implanting a specific element into the base material. This method is excellent in controllability of the concentration distribution in the depth direction. This permits implantation of catalysts with high accuracy. In addition to the ion implantation, thermal diffusion such as vapor-phase diffusion or solid-phase diffusion, and an implantation method with plasma may be employed.

In particular, when Pt is used as catalyst layer 336, aggregation of Pt particles can be reduced even at high temperatures. Since the diameter of fibrous substance 315 is dependent upon the particle diameter of the metal of catalyst layer 336, when Pt is used, finer fibrous substances 315 can be formed. Therefore, filtering performance is improved.

When a VSD (Vaporized substrate deposition) method or a VLS (Vapor Liquid Solid) method is used for a formation method of fibrous substance 315, in a state in which fibrous substance 315 is formed, the catalytic materials are present on the tip of fibrous substance 315 or on the surface of a base material directly joined to fibrous substance 315. When they are observed under electron microscope such as TEM, catalytic materials can be determined.

Figure 25:
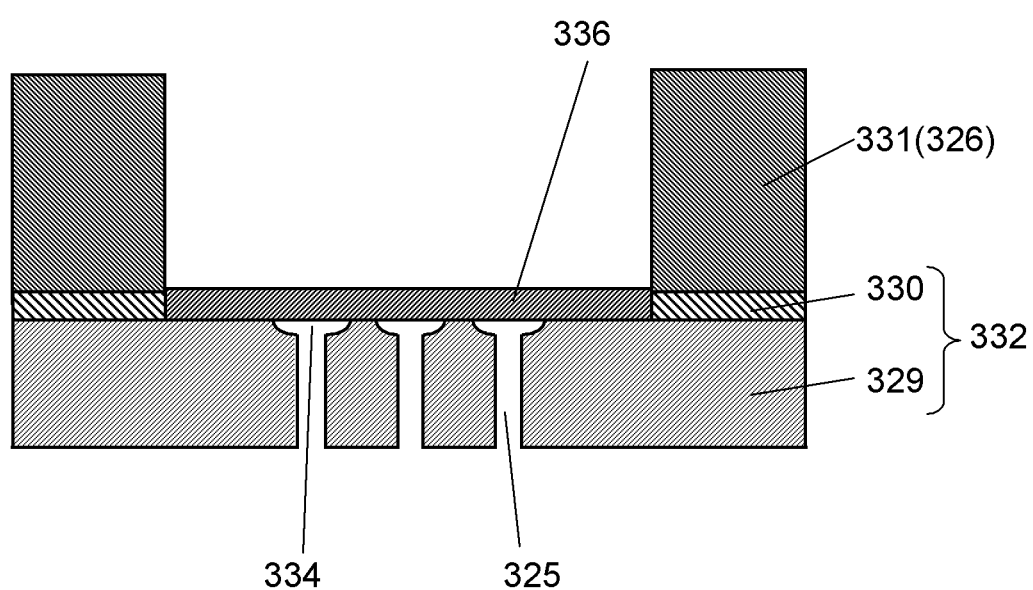
FIG. 25 is a sectional view showing a manufacturing step of the filter device in accordance with the third exemplary embodiment.

Next, as shown in FIG. 25, second resist mask 335 is washed and removed. At this time, catalyst layer 336 formed on the upper surface of second resist mask 335 is simultaneously washed. Thus, catalyst layer 336 can be selectively formed only on first surface 323 of silicon layer 329. At this time, previously formed first resist mask 332 can be washed and removed at the same time.

Figure 26:
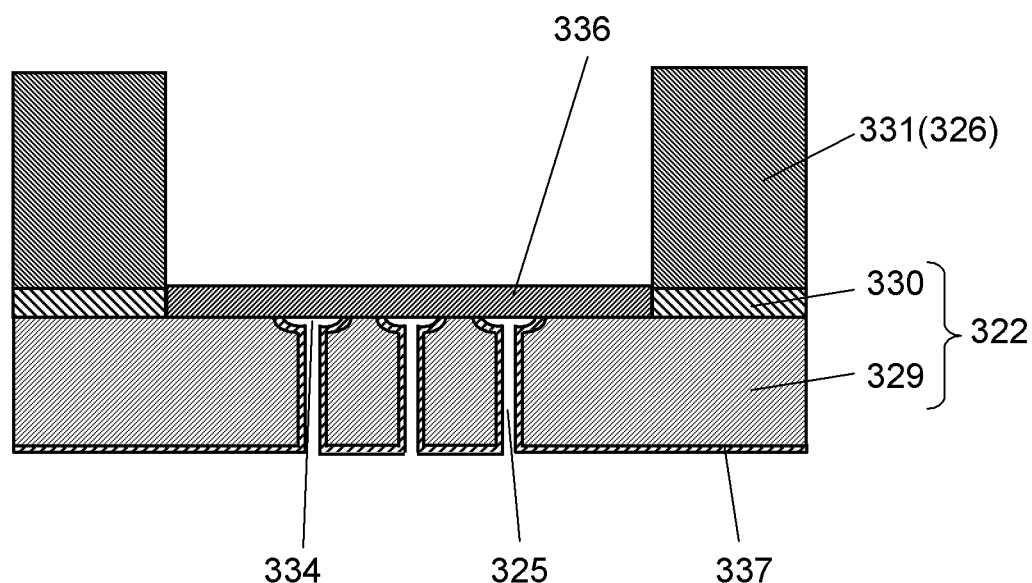
FIG. 26 is a sectional view showing a manufacturing step of the filter device in accordance with the third exemplary embodiment.

As shown in FIG. 26, filter chip 321 may be covered with protective film 337 such as a silicon dioxide film or a silicon nitride film in the periphery thereof, on at least a lower surface of silicon layer 329 and the inner wall surface of through-holes 325. Materials for protective film 337 include materials other than silicon, and desirably materials with high hydrophilic property. The materials with high hydrophilic property are materials having polarity or electric charge on the surface thereof.

By covering the periphery of filter chip 321 with protective film 337, it is possible to improve the hydrophilic property and to increase the strength of filter chip 321, and further to improve the patterning property of fibrous substance 315. This is because fibrous substance 315 can be allowed to grow selectively only on silicon.

When fibrous substance 315 is formed by the VSD method or the VLS method, when protective film 337 is used, fibrous substance 315 has more improved patterning property. As the materials of protective film 337, it is desirable to use materials having a higher vapor pressure than silicon or silicon monoxide. Examples of materials of protective film 337 are preferably inorganic oxide or inorganic nitride having a large difference in the vapor pressure from that of silicon, and the examples include silicon nitride, silicon oxynitride, aluminum oxide, and the like. By comprehensively considering these things, it is desirable that a material containing silicon dioxide as a main component is used as the protective film.

As a formation method using a silicon dioxide film as protective film 337, dry oxidization of introducing only an oxygen gas and carrying out oxidization is excellent in productivity. However, when the other methods are used, the same effect can be obtained. For example, in wet oxidation, oxygen gas and hydrogen gas are sent at a ratio of oxygen gas to hydrogen gas of 1:2, water vapor ($H_2O$) is made in the vicinity of introduction of furnace, and the water vapor is sent to the surface of silicon, thereby carrying out oxidization. Oxidization in the atmosphere in which halogen such as HCl or $Cl_2$ may be used. By these methods, when silicon dioxide films are formed as protective film 337, since growing speed of silicon dioxide differs depending upon the crystal orientation of the silicon layer, the shape of the opening portion of through-hole 325 is gradually changed from a circular shape to a rectangular shape.

Protective film 337 is not necessarily limited to a silicon dioxide film, and may be doped-oxide films such as a so-called PSG film doped with phosphorus, a so-called BSG film doped with boron, or a BPSG film doped with phosphorous and boron. Furthermore, silicon dioxide films formed by other methods such as a CVD method or a sputtering method or a CSD method may be employed.

Note here that protective film 337 may cover the entire places not only in the inner wall portions of through-hole 325, but also portions in which catalyst layer 336 is not formed, that is, a portion on which fibrous substance 315 is to be formed later. In such a case, the same effects can be obtained.

Furthermore, when protective film 337 is formed of a silicon dioxide film, by heat treating protective film 337 at temperatures of not lower than the softening point, the surface of protective film 337 starts to be melted, and the surface is made to be smooth (reflow).

At this time, the surface of the inner wall of through-hole 325 is a surface having an extremely excellent smoothness with the square mean roughness Rq of not more than 5.0 nm, which is difficult to be realized by usual etching. The square mean roughness Rq is defined by a square root of the square mean roughness of deviation from the mean value to the measurement value when the distribution of the surface roughness is measured.

When heat treatment is carried out and the surface of the inner wall of through-hole 325 is made to be smooth, the flow passage resistance is reduced. Therefore, even a specimen having low flexibility and elasticity can pass through through-hole 325.

A undoped silicon dioxide film formed by thermal oxidation has a relatively high softening temperature, 1160° C. However, the softening temperature of the PSG film is low, that is, the softening point is about 1000° C.; the softening temperatures of the BSG film and the BPSG film are low, that is, the softening points are about 900° C. Therefore, a reflow temperature can be reduced.

When a PSG film is used, the concentration of phosphorous is about 6 wt % to about 8 wt %. When the BPSG film is used, the dopant concentration is about 1 wt % to about 4 wt % for boron concentration, and about 4 wt % to about 6 wt % for phosphorous concentration. When the concentration of phosphorous is higher than about 7 wt % to about 8 wt %, phosphorous in the oxide and a water content in the air react with each other. Furthermore, when the boron concentration is higher than about 4 wt %, glass is unstable in high humidity.

Furthermore, when a silicon dioxide film formed by a CVD method is used as protective film 337, it has the softening point of around 1000° C., that is, the softening point that is lower than that of the silicon dioxide film formed by thermal oxidation, and it can be melted by heat of around 1000° C. Consequently, filter chip 321 with high accuracy can be made with energy saved.

Furthermore, the silicon dioxide film formed by the CVD method has also self-flattening property by the flowing of a polymerized product on the film surface at temperatures of not lower than 400° C.

As a raw material used in the formation by the CVD method, TEOS-$O_3$ is particularly excellent in the self-smoothness, but $SiH_4$—$O_2$, TEOS—$O_2$, or the like, which is a combination of SiH or TEOS and a gas functioning as an oxidizing agent, may be employed.

Whether the silicon dioxide film is formed by the CVD method or the thermal oxidation can be found by comparing the index of refraction or density. The silicon dioxide film formed by the CVD method has a refractive index of about 1.46, and the silicon dioxide film formed by thermal oxidation has a refractive index of about 1.48. The refractive indices are values measured by ellipsometry by using a He—Ne laser with a wavelength of 632.8 nm.

Furthermore, since it is difficult to directly measure the density of the silicon dioxide film, it can be analyzed from the etching rate of buffered hydrofluoric acid (BHF). When BHF (a solution obtained by adding 100 ml of solution, which contains 11 g of $NH_4F$ in 680 ml of $H_2O$, to 10 ml of 48% HF) is used, a silicon dioxide film by the CVD method has an etching rate of about 20 Å/min, and the etching rate of the silicon dioxide film by the thermal oxidation is about 6.8 to 7.3 Å/min.

When filter chip 321 is kept at a temperature that is not lower than the softening point, the shape of through-hole 325 approaches a perfect circle, but it changes depending upon conditions such as temperatures and time at which sensor chip 321 is kept, and the formation thickness of protective film 337. The larger the formation thickness of protective film 337 is, the stronger the tendency becomes. When the temperature at which filter chip 321 is kept is high or when the time for which filter chip 321 is kept is long, a large change in the shape occurs, and therefore the shape of through-hole 325 tends to be substantially a perfect circle. On the other hand, when the temperature at which filter chip 321 is kept is low or when the time for which filter chip 321 is kept is short, through-hole 325 has a shape in which the shape before heat treatment is relatively maintained.

Next, as shown in FIG. 27, by using a VSD method, filter portion 314 made of fibrous substances 315 is formed.

The VSD method is a method of introducing a base material on which a layer as a raw material of fibrous substance 315 and a catalytic metal material are formed on the surface layer thereof into a cylindrical furnace formed of ceramic and quartz. Fibrous substance 315 is selectively formed only on the raw material layer or on a catalytic metal.

A gas as a first raw material and a diluted gas (for example, $N_2$, Ar, and CO) are supplied from one end of the furnace, and exhausted from the other end. Furthermore, a base material having a second raw material and a catalytic metal material on the surface layer thereof is allowed to evaporate by heating at, for example, 1000° C. Thereafter, the second raw material is allowed to be absorbed by catalyst melted on the base material. Furthermore, the absorbed raw material is saturated in the catalyst and bonded to the first raw material, and thus fibrous substance 315 is formed.

When fibrous substance 315 including silicon dioxide is formed by the VSD method, the first raw material is oxidizable gas such as $O_2$, $O_3$, and $H_2O$, and the second raw material is a material containing silicon as a main component.

At this time, fibrous substance 315 is selectively formed on only a desired position provided with catalyst layer 336. The thickness of fibrous substance 315 can be controlled depending upon the conditions but it is generally 1 to 500 μm.

After silicon monoxide evaporates by heat treatment at high temperatures of 1000 to 1500° C. and at a low oxygen concentration, it adheres again and aggregates on the surface, and then silicon dioxide grows. At this time, silicon monoxide spreads over the surface of silicon of silicon layer 329, but it selectively adheres to a place on which catalyst layer 336 is formed, and is bonded to oxygen. Thus, fibrous substance 315 containing silicon dioxide as a main component grows. In the VSD method, it is an important to form silicon monoxide from a base material for forming fibrous substance 315.

Herein, the low oxygen concentration means that a partial pressure of oxygen at the time of heat treatment is low. It may be a reduced pressure in which the pressure of atmosphere is lowered from atmospheric pressure, and in which oxygen may be substituted by other gases. Examples of the other gases include $N_2$, Ar, and CO, which have low oxidization property unlike $O_2$, $O_3$, and $H_2O$. When the partial pressure of oxygen is too low, silicon monoxide cannot be generated. Desirable partial pressure of oxygen ranges from several thousands Pa to $10^{-2}$ Pa.

Herein, a method of manufacturing filter chip 321 in which filter portion 314 made of fibrous substances 315 is formed on first surface 323 of thin plate 322 made of silicon is described. However, by changing heat-treatment atmosphere, it is possible to select formation of fibrous substance 315 on only the upper surface of silicon layer 329 as shown in FIG. 25, or formation of fibrous substance 315 on only the upper surface of silicon dioxide layer 330 (not shown). When fibrous substance 315 is formed on only the upper surface of silicon dioxide layer 330, etching of silicon dioxide layer 330, which is carried out in the process shown in FIG. 23, is not necessary.

For example, when fibrous substance 315 is formed on only the upper surface of silicon dioxide layer 330, heat treatment needs to be carried out in the reducing atmosphere. The reducing atmosphere denotes an atmosphere in which gases such as $NH_3$, $H_2$, $N_2{}^+H_2$, CO, $H_2S$, $SO_2$, and HCHO (formaldehyde) are present.

Furthermore, a position on which catalyst layer 336 is formed can be arbitrarily changed depending upon positions on which first resist mask 332, second resist mask 335 and other resist masks are formed. That is to say, fibrous substance 315 can be formed on only places provided with catalyst layer 336, for example, only in through-holes 325, only on first surface 323 of thin plate 322, only on second surface 324 of second plate 322, only on both surfaces of thin plate 322, and the like. As a result, fibrous substance 315 can be formed on any positions of filter chip 321.

By combining them, fibrous substance 315 can be formed on any positions as shown in FIGS. 16 to 19.

However, as shown in FIG. 19, it is preferable that filter portion 314 made of fibrous substances 315 is formed inside holding portion 326. It is preferable in terms of the productivity because fibrous substance 315 is not easily peeled off.

Herein, a method of forming fibrous substance 315 by the VSD method using a base material as a raw material of fibrous substance 315 is described, but other formation methods can be selected. For example, a VLS method in which materials of fibrous substance 315 are supplied from others or an electrospinning method may be used.

The VLS method is a method of allowing fine droplets of liquid catalytic metal to absorb vapor-phase semiconductor raw materials, and then precipitating solids of a semiconductor eutectic product under the droplets. A catalytic metal is selectively formed on fibrous substance 315.

The VLS method mainly uses an electric furnace device called a two-zone furnace. The two-zone furnace includes a cylindrical furnace made of ceramic or quartz, in which an upstream side region and a downstream side region can be heated at different temperatures.

When fibrous substance 315 is formed by the VLS method, a gas as the first raw material and a diluted gas (for example, $N_2$, Ar, and CO) are supplied from one side of the furnace, and exhausted from the other end. The upstream side region contains the second raw materials as solid powder, and the upstream side region is heated at, for example, at 1000° C. so as to evaporate the second raw material. The downstream side region contains a base material including a surface layer made of a catalytic material including metal, and is heated at a temperature at which the catalytic metal formed on the substrate is melted, for example, at 500° C. Then, the second raw material evaporated in the upstream side region is allowed to be absorbed by the melted metal on the substrate. When the absorbed raw material is saturated in the metal, it is bound to the first raw material, and thereby fibrous substance 315 is formed.

In this case, similar to the VSD method, when fibrous substance 315 including silicon dioxide is formed, the first raw material is oxidizable gas such as $O_2$, $O_3$, and $H_2O$, and the second raw material is a material containing silicon as a main component.

In addition, an elector spinning method can be used to form fibrous substance 313. The electro spinning method uses a device including a high voltage power supply, a polymer solution storage tank, a spinning head, and an earthed collector. A polymer solution is extruded from the tank to the spinning head at a constant speed. At the spinning head, a voltage of 10 to 30 kV is applied, and when the electric attractive force exceeds the surface tension of the polymer solution, a jet of the polymer solution is sprayed toward the collector. At this time, a solvent in the jet is gradually volatilized, and the size of the jet is reduced to the nano-level when the jet reaches the collector, and fibrous substance 315 is formed. The polymer solution used when fibrous substance 315 including silicon dioxide is obtained, a mixture of tetra-ethoxysilane (TEOS) with ethanol, purified water and hydrogen chloride is generally used.

In this exemplary embodiment, since a base material including silicon is used for thin plate 322, the VSD method is desirable because it is a simple, does not need an expensive device, and is excellent in the patterning property. Furthermore, since fine and bending fibrous substances 315 can be obtained as compared with the other methods, it is possible to obtain filter device 300 having high properties.

It is possible to determine that fibrous substance 315 is formed from silicon by the VSD method because concavity and convexity according to the crystal plane orientation remain on the upper surface (first surface 323) of silicon layer 329 on which catalyst layer 336 has been formed.

Note here that when a plurality of filter chips 321 are simultaneously formed by one substrate, filter chip 321 is required to be separated individually.

Examples of the shape of the upper part of filter chip 321 include a square, a parallelogram, a rectangle, a circle, and an ellipse. Among them, the circle is preferable from the viewpoint of productivity because a general glass tube or a tube can be used. In this case, workability of blade dicing is reduced. However, when dicing with laser or etching between filter chips 321 is used, the workability of filter chip 321 is improved, and arbitrary shapes can be selected.

In particular, the use of dicing with a laser makes it possible to carry out processing with a high speed, less chipping, and high transverse rupture strength. In this case, the thickness and the size of filter chip 321 can be reduced. Processing by laser dicing can be determined by thermal effect, debris contamination, occurrence of cracks perpendicular to the surface direction of filter chip 321, or the like.

Figure 28:
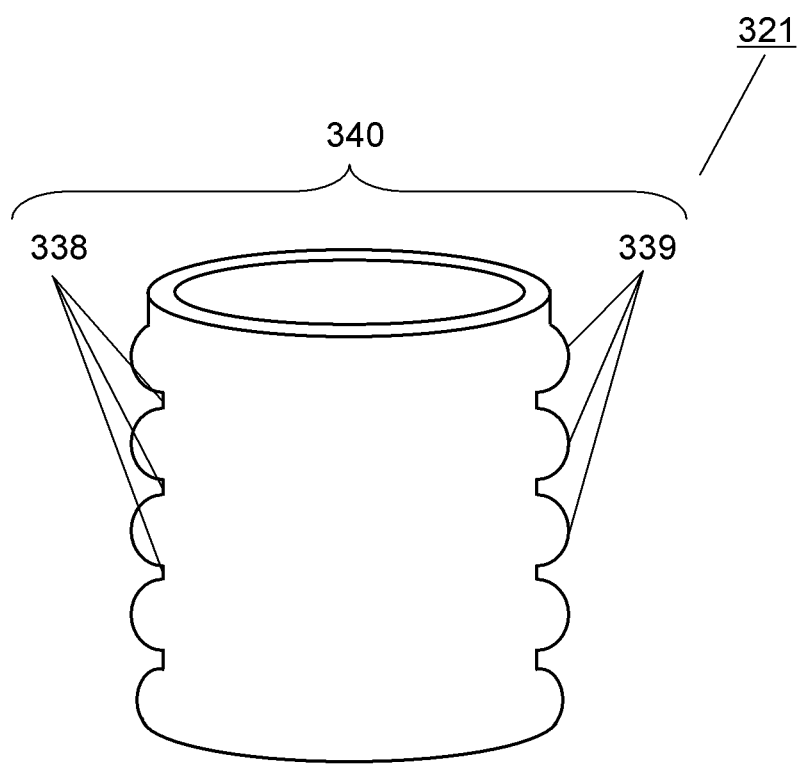
FIG. 28 is an enlarged perspective view of a part of the filter device in accordance with the third exemplary embodiment.

FIG. 28 is an enlarged perspective view of a part of the filter device in accordance with this exemplary embodiment, in which filter chip 321 is separated individually by etching. When individual units are separated by etching, as shown in FIG. 28, a trace of etching is generated on the outer wall surface of filter chip 321. In particular, since etching is carried out by repeating a cycle including etching and deposition, the outer peripheral shape of the side surface of the outer wall surface of filter chip 321 in this case is a stepped shape called scallop provided with concave and convex portion 340 including annular concave portion 338 and annular convex portion 339. The step of the scallop is in the order of several nm to several tens nm. Furthermore, it is desirable that the outer wall surface of filter chip 321 has the above-mentioned step shape because a surface area per unit length in which capillary 320 and filter chip 321 are joined to each other is increased and adhesive property is improved.

Etching into individual units is desirable from the viewpoint of productivity because it can be carried out at the same time when etching in FIGS. 22 and 23 is carried out.

Next, thus formed filter chip 321 is inserted into capillary 320.

A method of inserting filter chip 321 is not particularly limited, but a method of filling liquid in capillary 320, and sucking filter chip 321 by a capillary phenomenon is preferable.

As capillary 320, for example, glass can be used.

Filter chip 321 and capillary 320 are joined to each other by exposing glass as capillary 320 to fire by using a burner so as to melt glass to be fused to filter chip 321. In this case, as a material for volatilizing a liquid to be filled, for example, water is used. Thus, filter chip 321 and capillary 320 are directly joined to each other. The "directly joined" means a case where a covalent linkage is generated between filter chip 321 and capillary 320. Furthermore, a method in which joining is carried out by activating the joined surface by anodic joining or with Ar, or a method in which joining is carried out by SiON bond by combining between $O_2$ plasma and $N_2$ plasma may be employed. In this case, materials having a relatively low melting point can be used for filter chip 321 or capillary 320.

In addition to the above-mentioned joining method, by using an adhesive layer (not shown), filter chip 321 can be joined to capillary 320.

Materials for the adhesive layer are not particularly limited, but adhesive resin such as polydimethylsiloxane (PDMS) or UV hardened resin, inorganic materials such as $SiO_2$, metal material such as Au, and the like, may be used. When a metal material is used as an adhesive layer, eutectic join, Au—Au join and the like can be used.

Note here that filter chip 321 may be inserted in such a manner that holding portion 326 is located in the lower part.

Hereinafter, advantageous effects of filter device 300 of this exemplary embodiment are described.

In filter device 300 of this exemplary embodiment, filter chip 321 portion is not required to be covered with a lid or the like. Furthermore, since fibrous substance 315 can be certainly formed on a portion through which a solution passes with substantially the same density, filtration products flowing in capillary 320 can be removed efficiently.

Since filter chip 321 portion is not required to be sealed by forming a lid, it is possible to reduce the number steps for producing filter device 300.

Furthermore, since fibrous substance 315 is formed in a state in which it is directly joined to thin plate 322 (base material), the structural strength is great. Since fibrous substances 315 with a high aspect ratio are entangled with each other and closely gathered so as to form filter portion 314, fibrous substances 315 can include gaps in the multiple directions. This makes it possible to adsorb filtration products from various angles, and to improve the reliability of filter portion 314. Furthermore, with the above-mentioned configuration, gaps between fibrous substances 315 are fine, and specimens and filtration products can be separated easily, and only specimens can be extracted without carrying out surface treatment.

Furthermore, in the method of manufacturing fibrous substance 315 in this exemplary embodiment, since fibrous substance 315 is formed after the separation process, etching treatment is not carried out after fibrous substance 315 is formed. Accordingly, fibrous substances 315 are not broken. Therefore, the reliability of filter portion 314 can be improved.

Furthermore, since filter chip 321 is formed such that the upper part is formed in a circular shape, it can be easily connected to capillary 320 that usually has a circular cylindrical shape, for example, a glass tube or a rubber tube.

Furthermore, by fixing a tip of capillary 320 of filter device 300 to a vessel containing a living body test material, the living body test material can be directly introduced into a flow passage. Therefore, it is not necessary to use an additional connector.

Furthermore, since fixing a tip of capillary 320 of filter device 300 to a vessel containing a living body test material can be carried out by simple operation, an operation is facilitated.

Fourth Exemplary Embodiment

Hereinafter, a filter device in accordance with a fourth exemplary embodiment of the present disclosure is described with reference to drawings.

In this exemplary embodiment, the same reference numerals are given to the same configurations as in the third exemplary embodiment, and detailed description thereof may be omitted.

This exemplary embodiment is different from the third exemplary embodiment in which an SOI substrate is used as a base material for forming filter chip 421, all of a silicon layer is used as a raw (source) material for fibrous substance 415, fibrous substance 415 is formed by consuming all of the silicon layer, and thereby the formed fibrous substance 415 and silicon dioxide layer 430 are directly joined to each other.

Figure 29:
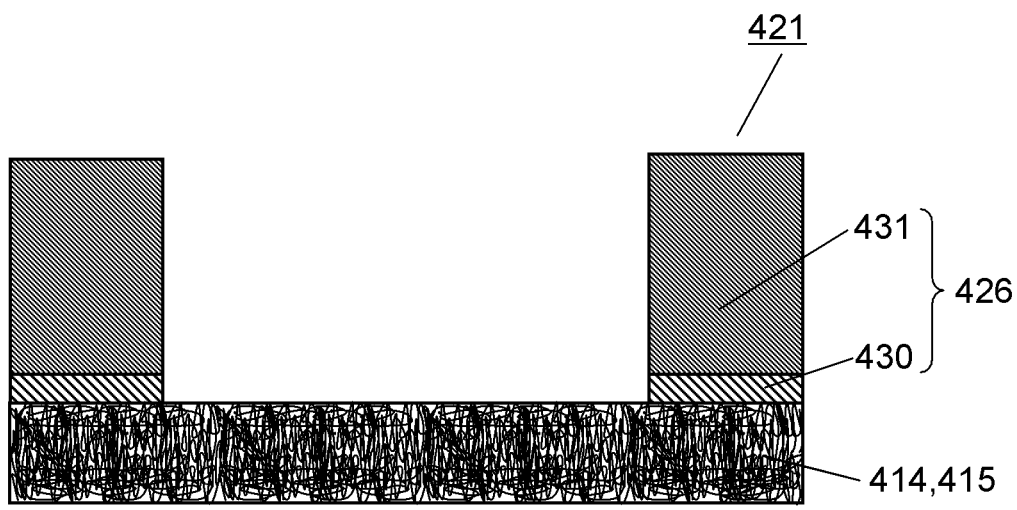
FIG. 29 is an enlarged sectional view of a part of a filter device in accordance with a fourth exemplary embodiment of the present disclosure.
Figure 30:
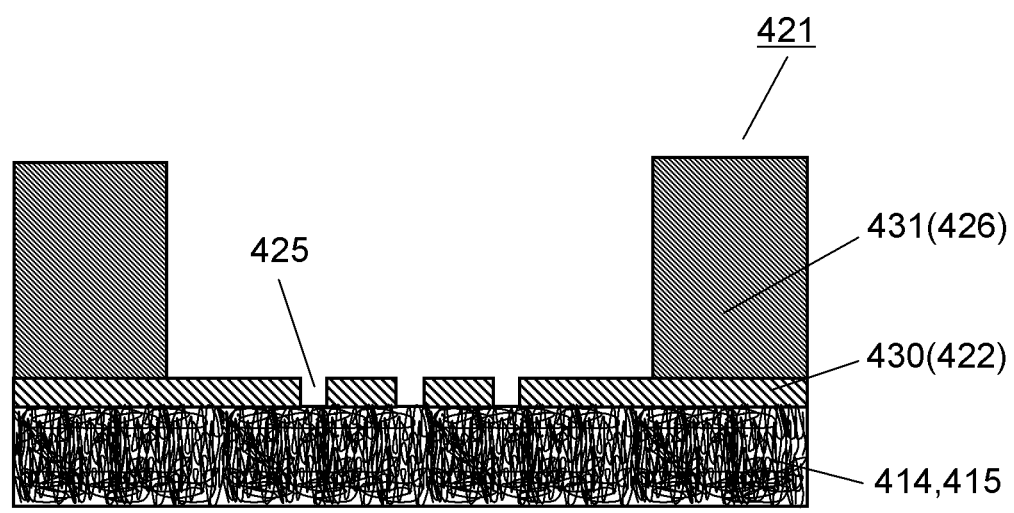
FIG. 30 is an enlarged sectional view of a part of the filter device in accordance with the fourth exemplary embodiment.

FIGS. 29 and 30 are enlarged sectional views of a part of a filter device in this exemplary embodiment.

As shown in FIG. 29, in filter chip 421 of this exemplary embodiment, filter portion 414 made of fibrous substances 415 directly joined to the lower surface of silicon dioxide layer 430 is formed. In this case, an SOI substrate is used and silicon layer 431 and silicon dioxide layer 430 are etched so as to form holding portion 426. Thereafter, a catalyst layer (not shown) is formed only on the lower surface of the silicon layer (not shown). By using the VSD method when fibrous substance 415 is formed, the silicon layer (not shown) is consumed and fibrous substance 415 can be formed.

With the above-mentioned configuration, since fibrous substance 415 formed not parallel to each other but entangled with each other is joined to silicon dioxide layer 430, it is possible to suppress peeling of fibrous substance 415 from filter chip 421. Thus, it is possible to maintain the strength of filter portion 414 made of fibrous substances 415.

Furthermore, filter chip 421 does not include a thin plate, and is formed of only fibrous substance 415. Consequently, a filter that facilitates observation of a filtration product can be obtained.

In the manufacturing method of this exemplary embodiment, since all of the silicon layer (not shown) is consumed for forming fibrous substance 415, fibrous substance 415 may not be broken. That is to say, when a filter chip is made by previously forming a fibrous substance and then forming through holes or a concave portion by, for example, etching, the fibrous substance may be broken by etching. However, when the filter chip is formed by the manufacturing method of this exemplary embodiment, since fibrous substance 415 is formed in the final step, it is possible to prevent fibrous substance 415 from being broken by etching.

Furthermore, since all of the silicon layer (not shown) is a raw material of fibrous substance 415, as compared with the third exemplary embodiment, it is not necessary to include a step of forming through holes in a silicon layer (not shown) by etching, or a step of covering the inner wall of the through hole with a protective film. Thus, the productive efficiency is improved.

As the thickness of the silicon layer (not shown) as a raw material is larger, the more fibrous substances 415 can be formed. Therefore, a filter effect can be improved. Also in such a case, in order to maintain the strength of filter chip 421 itself, it is preferable that the thickness of silicon dioxide layer 430 is not less than 5 μm.

As shown in FIG. 30, thin plate 422 made of silicon dioxide layer 430 and having through holes 425 is formed, and fibrous substance 415 is directly joined to be formed on the lower surface of thin plate 422.

In this case, an SOI substrate is used, and silicon layer 431 is etched from the upper part of the SOI substrate to form holding portion 426, and then through holes 425 are formed in a silicon layer (not shown) and silicon dioxide layer 430 from the lower part of the SOI substrate. Thereafter, a catalyst layer (not shown) is formed only on the lower surface of silicon layer 431. When fibrous substance 415 is formed by using the VSD method, silicon layer 431 is consumed and fibrous substance 415 can be formed. With the above-mentioned manufacturing method, thin plate 422 formed of only silicon dioxide layer 430 and having through holes 425 can be formed.

Note here that it is also possible to form fibrous substance 415 so as to cover silicon dioxide layer 430 and a part below the plurality of through holes 425 formed in silicon dioxide layer 430.

In the above-mentioned configuration, since a thin plate is formed of a silicon dioxide layer, that is, formed of permeable materials, it is possible to obtain a filter that facilitates observation of a filtration product.

Fifth Exemplary Embodiment

Hereinafter, a filter device in accordance with a fifth exemplary embodiment of the present disclosure is described with reference to drawings.

Figure 31:
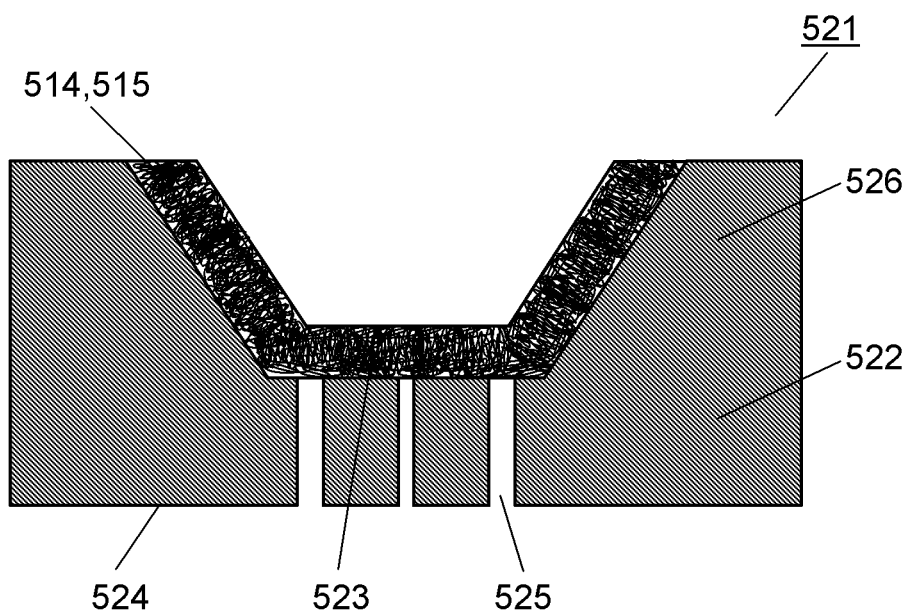
FIG. 31 is an enlarged sectional view of a part of a filter device in accordance with a fifth exemplary embodiment of the present disclosure.

FIG. 31 is an enlarged sectional view of a part of the filter device in accordance with this exemplary embodiment.

In this exemplary embodiment, the same reference numerals are given to the same configurations as in the first and third exemplary embodiments, and detailed description thereof may be omitted.

This exemplary embodiment is different from the first to fourth exemplary embodiments in that filter chip 521 includes holding portion 526 provided with a taper.

As shown in FIG. 31, filter chip 521 of this exemplary embodiment includes thin plate 522, and a plurality of through holes 525. Thin plate 522 includes silicon as a main component. The plurality of through holes 525 penetrate through first surface 523 and second surface 524 opposite to first surface 523 of thin plate 522. Furthermore, fibrous substance 515 is provided so as to cover first surface 523 and portions above the opening portions of plurality of through holes 525 opened in first surfaces 523. Fibrous substance 515 includes amorphous silicon oxide.

Furthermore, filter chip 521 includes holding portion 526 for holding thin plate 522.

Holding portion 526 is provided with a taper that becomes narrower from the upper surface of holding portion 526 toward a plate-like thin plate 522. When the taper is provided, specimens can be collected more efficiently into the periphery of through holes 525. As a result, filter chip 521 can improve the speed of filtering specimens.

As a base material for producing filter chip 521, a silicon single crystal substrate including silicon (100) is used. The orientation of the silicon single crystal substrate is not particularly limited. However, from the viewpoint of the workability or the versatility, it is preferable to use a substrate including silicon (100).

When holding portion 526 formed of silicon is formed by etching with an alkaline solution, from the difference in the etching rate by the orientation of silicon, the shape of holding portion 526 becomes a pyramid shape surrounded by silicon (111) planes. At this time, angle X made by the side surface of holding portion 526 and plate-like thin plate 522 is about 54°.

Therefore, it is desirable that through holes 525 are comprehensively arranged by considering an angle made by the side surface of holding portion 526 and plate-like thin plate 522 as well as a dimension of the opening portion in the upper surface of holding portion 526.

Figure 39:
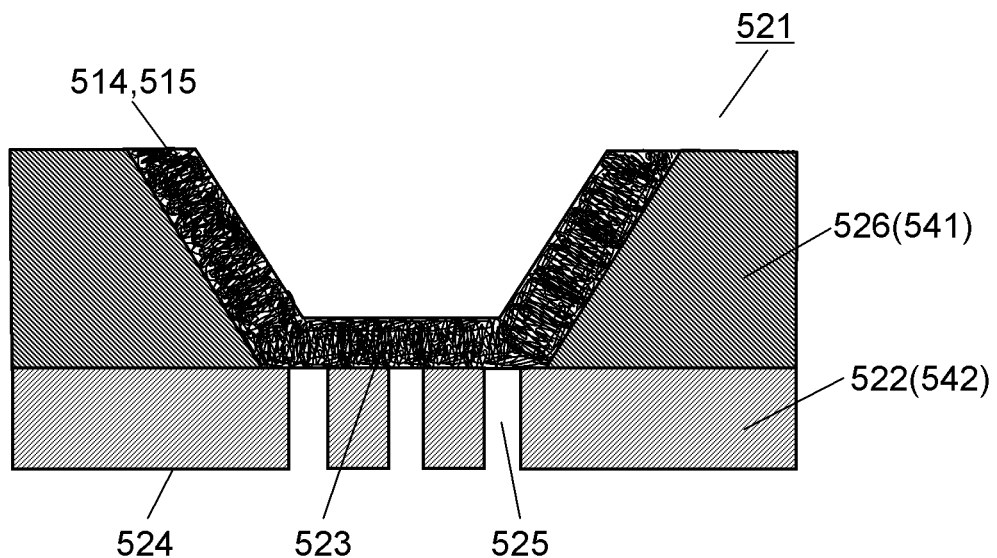
FIG. 39 is an enlarged sectional view of a part of the filter device in accordance with the fifth exemplary embodiment.

Furthermore, as shown in FIG. 39, as a base material for producing filter chip 521, it is possible to use a base material on which doped layer 542 obtained by doping silicon with boron at high concentration is formed on the upper surface (the lower surface in FIG. 39) in the thickness direction of silicon layer 541 containing as a main component. In this case, doped layer 542 is used as thin plate 522 and silicon layer 541 is used as holding portion 526.

When an alkaline solution is used for wet-etching of doped layer 542, the etching speed of doped layer 542 is reduced in approximately proportion to the power of four of the boron concentration. Therefore, when silicon layer 541 is wet-etched with an alkaline solution, doped layer 542 functions as a stop layer. Thus, the shape of filter chip 521 can be controlled with high accuracy.

Furthermore, when boron is used as dopant of the doped layer 542, the thickness thereof is 1 to 30 μm, the boron concentration is not less than $2 \times 10^{19}$ cm$^3$. For implanting a boron element into silicon, an ion implantation method is suitably used. The ion implantation method is a method of electrically accelerating ions and allowing ions to collide with an object, thereby implanting a specific element into the substrate. This method is excellent in controllability of the concentration distribution in the depth direction. This permits addition of desired element with higher accuracy. In addition, other methods such as an implantation method using plasma, and thermal diffusion such as vapor phase diffusion or solid phase diffusion can be used. When these implantation methods of elements are carried out, concentration gradient occurs in the elements which are added to the inside of silicon.

In this exemplary embodiment, boron is used for doped layer 542. However, silicon doped with elements such as germanium, phosphorus, and other elements, which reduce the etching rate with respect to an alkaline solution, or the combination thereof, may be used as doped layer 542.

However, doped layer 542 is not necessarily required to be formed, and it is possible to stop etching by time management for etching treatment.

When doped layer 542 doped with boron is used, when etching with an alkaline solution is carried out, linear patterns are generated in which parallel stripes are orthogonal to the silicon (110) direction. This is generated due to high tensile stress occurring in doped layer 542.

The following is description of a manufacturing method in this exemplary embodiment, which uses, as a base material for producing filter chip 521, a silicon (100) single crystal substrate on which a boron-doped layer is formed as doped layer 542 on the upper surface in the thickness direction of silicon layer 541 containing silicon as a main component.

FIGS. 32 to 38 are sectional views each showing a manufacturing step of the filter device in accordance with this exemplary embodiment.

Figure 32:
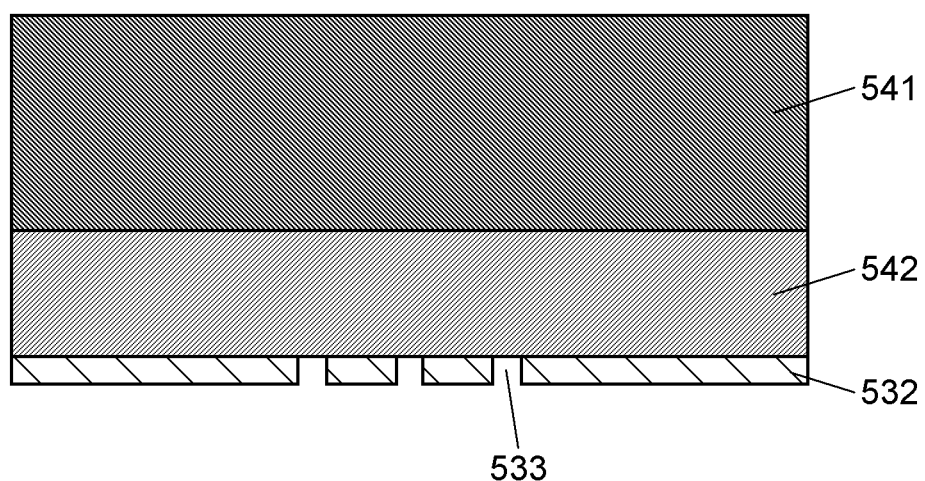
FIG. 32 is a sectional view showing a manufacturing step of the filter device in accordance with the fifth exemplary embodiment.

As shown in FIG. 32, first resist mask 532 is formed with respect to the upper surface (a lower surface in FIG. 20) of doped layer 542 formed on one plane of a base material by a conventional photolithography technique. When a plurality of filter chips are simultaneously formed by one base material, a plurality of mask holes 533 having substantially the same shapes as the lateral sectional surfaces of desired through holes are patterned with respect to individual filter chips.

Figure 33:
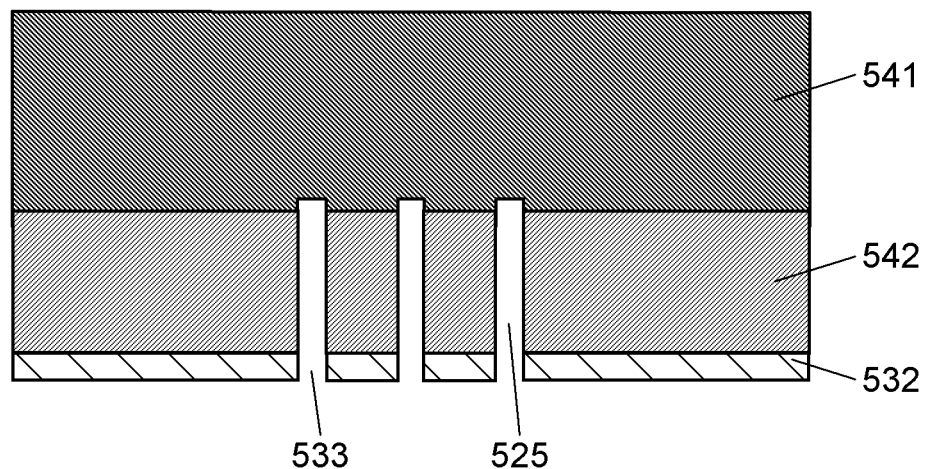
FIG. 33 is a sectional view showing a manufacturing step of the filter device in accordance with the fifth exemplary embodiment.

Next, as shown in FIG. 33, the base material is etched from mask hole 533 side of doped layer 542 so as to form through holes 525. As the etching method, dry etching capable of fine processing with high accuracy is desirable. When dry etching is carried out, in order to form through hole 525 with a high aspect ratio (with large depth with respect to the hole diameter), an etching gas for promoting etching and a suppressing gas for suppressing etching are alternately used.

In this exemplary embodiment, $SF_6$ is used as the etching gas, and $C_4F_8$ is used as the suppressing gas. Through hole 525 is formed in a length that is not shorter than the thickness of doped layer 542. That is to say, through hole 525 is formed such that it reaches not only doped layer 542 but also silicon layer 541, and reaches a part of silicon layer 541. In general, deep and vertical through hole 525 having a depth of 1 to 50 µm is formed.

Note here that first resist mask 532 may be removed at this time, but, from the viewpoint of efficiency, it is preferably removed at the same time when a second resist mask that is to be produced later is removed.

Figure 34:
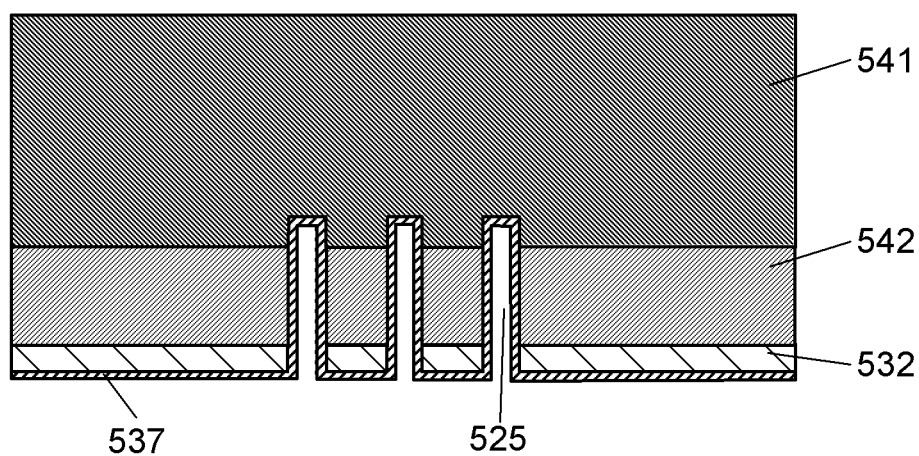
FIG. 34 is a sectional view showing a manufacturing step of the filter device in accordance with the fifth exemplary embodiment.

Next, as shown in FIG. 34, the inside of through holes 525 and the upper surface of first resist mask 532 (the lower surface in FIG. 34) are covered with protective film 537 made of silicon dioxide by using, for example, a CVD method. As protective film 537, in addition to silicon dioxide, any materials and formation method are not particularly limited as long as the materials contain silicon dioxide as a main component and materials are made of a silicon nitride film and the like and having resistance to alkaline etching. Examples of the materials containing silicon dioxide as a main component include doped oxide films such as a so-called PSG film obtained by doping silicon dioxide with phosphorus, a so-called BSG film obtained by doping silicon dioxide with boron, or a BPSG film obtained by doping silicon dioxide with phosphorous and boron. Furthermore, protective film 527 can be formed by other methods such as a sputtering method, and a CSD method, may be employed in addition to the CVD method. When the silicon nitride film is used as protective film 537, when protective film 537 has a thickness of not less than several nm, it has sufficient resistance with respect to alkaline etching.

Herein, it is not indispensable to cover the inside through holes 525 with protective film 537. However, in particular, when doped layer 542 is not formed, in order to make the shape of filter chip 521 highly accurately, it is desirable that protective film 537 is formed.

If necessary, protective film 537 may be heated to a temperature of not lower than the softening point. By heating a temperature to not lower than the softening point, the surface of protective film 537 starts to be melted, and the surface is smoothed (not shown).

Figure 35:
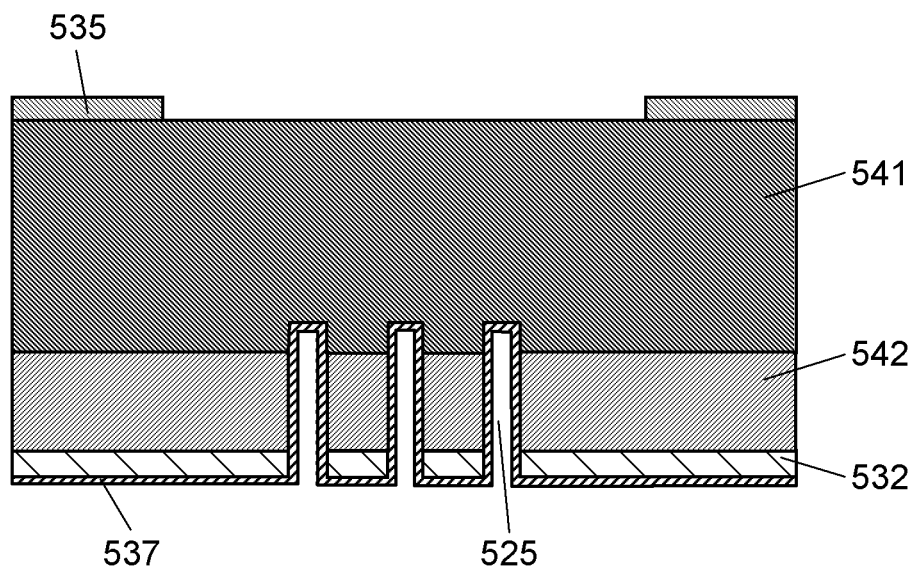
FIG. 35 is a sectional view showing a manufacturing step of the filter device in accordance with the fifth exemplary embodiment.

Next, as shown in FIG. 35, by using conventional photolithography technique, second resist mask 535 is formed on silicon layer 541, that is, a surface opposite to doped layer 542 of the substrate (an upper surface in FIG. 35).

Figure 36:
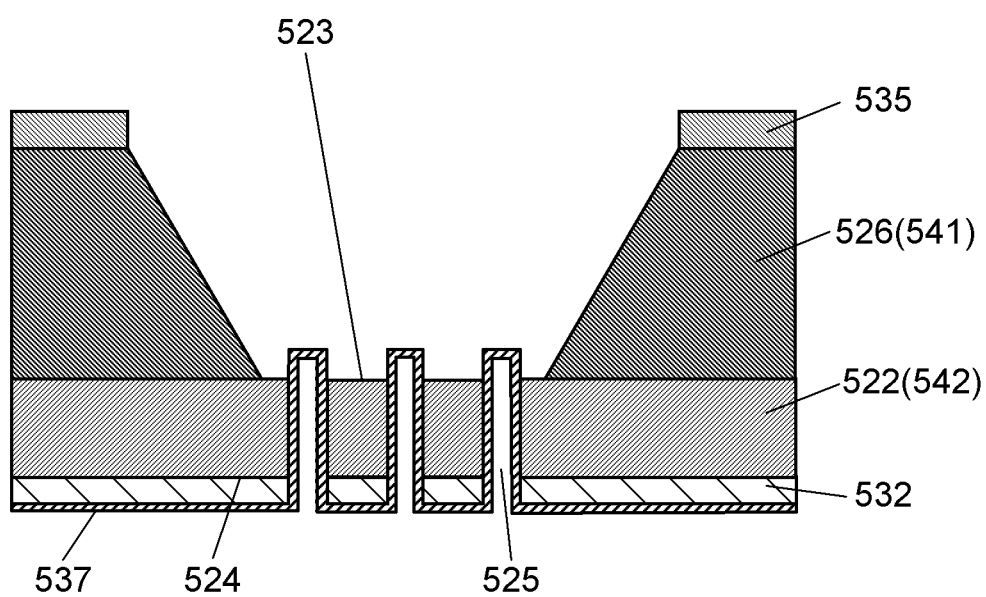
FIG. 36 is a sectional view showing a manufacturing step of the filter device in accordance with the fifth exemplary embodiment.

Then, as shown in FIG. 36, by using anisotropic wet etching with an alkaline solution such as KOH or TMAH solution, holding portion 526 is formed from second resist mask 535 side. The depth of holding portion 526 can be controlled by the etching time. In this exemplary embodiment, by using doped layer 542 as thin plate 522 of filter chip 521, when wet etching of silicon layer 541 with an alkaline solution is carried out, an etching stop can be determined. As a result, the shape of filter chip 521 can be controlled with high accuracy.

With this etching, from the difference in the etching rate by the orientations of silicon, the shape of holding portion 526 can be made into a pyramid shape surrounded by silicon (111) planes. At this time, angle X made by the side surface of silicon layer 541 and doped layer 542 is about 54°.

In the case of silicon wet etching with an alkaline solution, the etching speed generally satisfies the relation: silicon (100)>silicon (110)>>silicon (111). In other words, a pyramid shape of holding portion 526 has a square shape in which one side of the upper surface of the pyramid shape is one side in the (110) direction when it is seen in the vertical direction with respect to the base material surface. With wet etching of silicon with an alkaline solution, a plurality of layers can be treated at one time and a device can be simplified, and furthermore make it possible to use a base material including doped layer 542. Thus, the base material including doped layer 542 can be obtained at low cost as compared with an SOI substrate, and therefore, it has a merit also in terms of cost.

For wet etching of silicon with an alkaline solution, hydroxide of alkaline metal such as KOH, EDP (a mixture of ethylenediamine, pyrocatechol and water), TMAH, NaOH, CsOH, $NH_4OH$, hydrazine, or the like, is used. A standard composition of EDP includes 133 mL of water, 1 L of ethylenediamine, 160 g of pyrocatechol, and 6 g of pyrazine.

Among them, KOH is desirable because the etching speed of doped layer 542 becomes smaller as compared with that of the other composition, and the shape of a chip with high accuracy can be obtained.

Furthermore, silicon (100) is etched with KOH having low to middle concentrations (not higher than 10 mol/L, for example, about 4 mol/L) or EDP, the surface tends to be a rough surface. On the other hand, by using a KOH solution having a high concentration (not lower than 10 mol/L), it is possible to obtain (100) plane that is near a mirror surface. Thus, it is possible to obtain filter chip 521 having small flow passage resistance.

Note here that KOH has a relatively small selection ratio with respect to silicon dioxide to be used as protective film 537, the etching rate by KOH of silicon layer 541 and silicon dioxide is 150:1. That is to say, when 300 µm-thick silicon layer 541 is etched, the thickness necessary for protective film 537 is about 2 µm.

In order to suppress etching by long-time exposure of protective film 537 including silicon dioxide to KOH, the thickness of protective film 537 needs to be increased. When it is difficult to increase the thickness of protective film 537 in terms of production, EDP instead of KOH is desirably used. Since the etching speed of silicon dioxide with EDP is about 1/100 of that with KOH, etching of protective film 537 can be suppressed as compared with the case where KOH is used.

Besides, holding portion 526 can be formed by using gas etching capable of etching silicon with $SF_6$, $CF_4$, $Cl_2$, $XeF_2$, or the like. However, in these cases, difference in the etching rate due to the orientations of silicon, holding portion 526 does not have a clear pyramid shape but has a relatively round shape.

In particular, in order to form a taper shape in which an opening portion becomes narrower from the upper surface of holding portion 526 toward thin plate 522 formed of doped layer 542, it is desirable to use RIE (Reactive Ion Etching) using these gases.

When it is necessary to control the taper shape with high accuracy, similar to FIG. 21, etching of alternately using an etching gas and a suppressing gas may be employed.

As shown in FIG. 36, after holding portion 526 is formed by wet etching, protective film 537 may be removed. In particular, as shown in FIG. 34, when protective film 537 covers also silicon layer 541, through holes 525 are closed by protective film 537. Therefore, it is desirable that protective film 537 is removed at this time.

Figure 40:
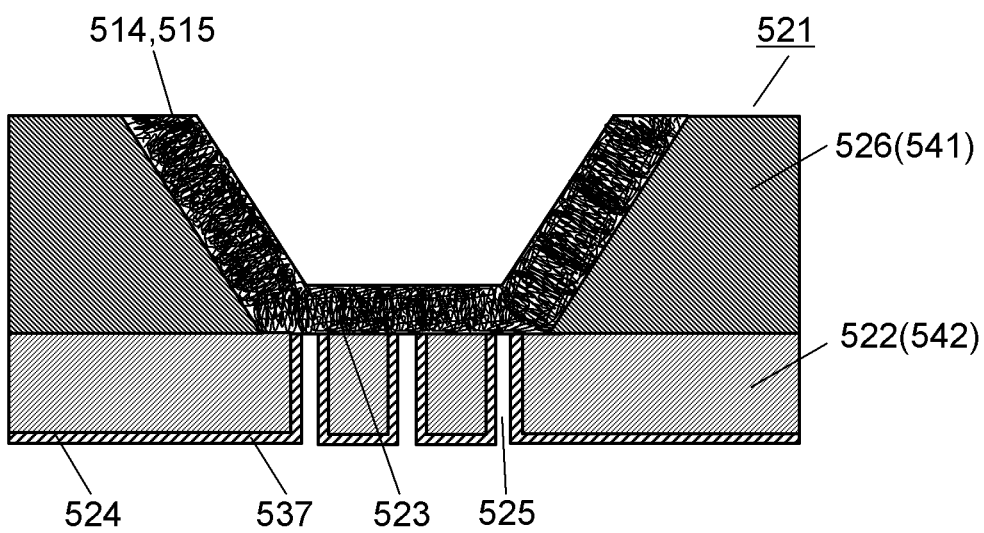
FIG. 40 is an enlarged sectional view of a part of the filter device in accordance with the fifth exemplary embodiment.

Furthermore, also by carrying out heat treatment to temperatures of not lower than the softening point of protective film 537, protective film 537 closing through holes 525 can be removed. This is because heat treatment at a temperature that is not lower than the softening point of protective film 537, protective film 537 is melted, and the shape of protective film 537 is changed along the shape of through holes 525 formed in silicon layer 541. Thus, similar to the third exemplary embodiment, it is possible to obtain filter chip 521 in which protective film 537 is formed on the inner wall of through hole 525 as shown in FIG. 40. Note here that when resist mask 532 is removed before protective film 537 is formed, protective film 537 is provided on also on second surface 524 of thin plate 522.

Figure 37:
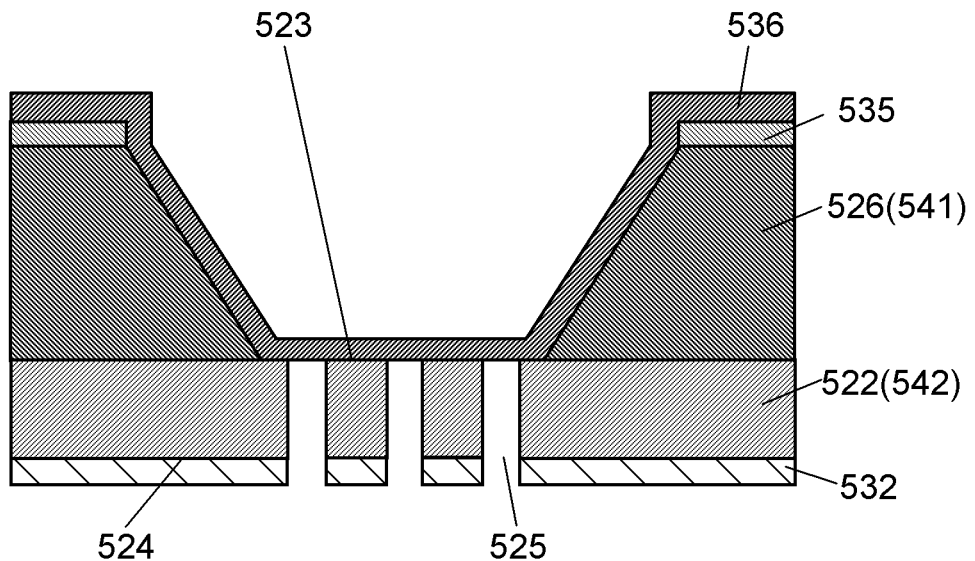
FIG. 37 is a sectional view showing a manufacturing step of the filter device in accordance with the fifth exemplary embodiment.

Next, as shown in FIG. 37, catalyst layer 536 is formed from first surface 523 of thin plate 522 (an upper surface in FIG. 37), that is, from a portion above through holes 525. At this time, in a region in which second resist mask 535 is formed, catalyst layer 536 is formed on the upper surface of second resist mask 535.

Figure 38:
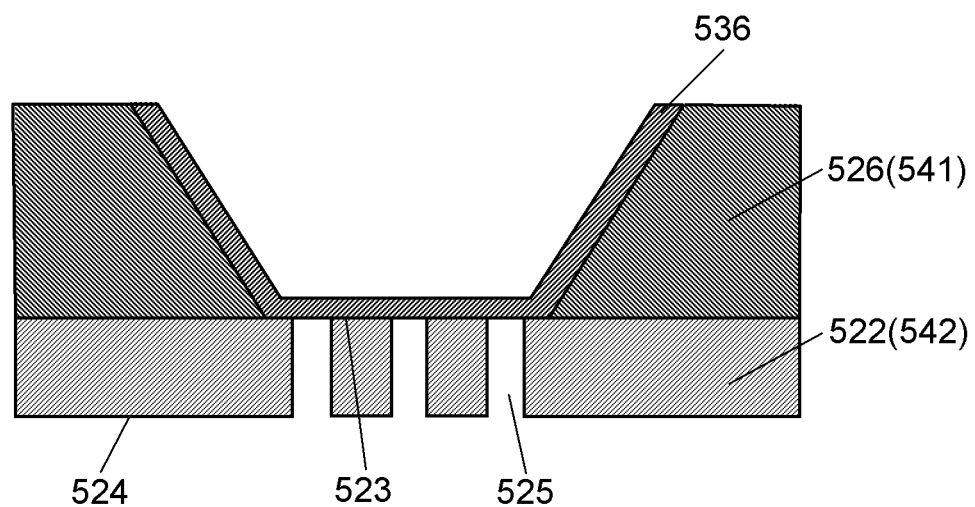
FIG. 38 is a sectional view showing a manufacturing step of the filter device in accordance with the fifth exemplary embodiment.

Next, as shown in FIG. 38, second resist mask 535 is washed to be peeled off. At this time, catalyst layer 536 formed on the upper surface of second resist mask 535 is washed simultaneously. This makes it possible to form catalyst layer 536 selectively only on first surface 523 of thin plate 522 and on the inner wall of holding portion 526. At this time, the previously formed first resist mask 532 can be washed to be peeled off at the same time.

FIGS. 39 and 40 are enlarged sectional views each of a part of the filter device in accordance with this exemplary embodiment.

Next, as shown in FIG. 39, fibrous substance 515 is formed by using the VSD method. At this time, fibrous substance 515 is selectively formed only on a position on which catalyst layer 536 is formed. In this case, fibrous substance 515 covers not only the upper surface of first surface 523 of thin plate 522 and the portions above the opening portions of through holes 525 opened in first surfaces 523, but also the inner wall surface of holding portion 526. Therefore, filter chip 521 can exhibit a further improved filter effect.

Similar to the third exemplary embodiment, a position on which catalyst layer 536 is formed can be arbitrarily changed depending upon positions on which first resist mask 532 and second resist mask 535 are formed. That is to say, fibrous substance 515 can be formed only on positions on which catalyst layer 536 is formed, for example, only on the inner walls of through holes 525, only on first surface 523 of thin plate 522, only on second surface 524 of thin plate 522, on both surfaces of thin plate 522 (that is to say, first surface 523 and second surface 524 of thin plate 522). Therefore, it is possible to form fibrous substance 515 in any arbitrary positions.

Furthermore, as shown in FIG. 40, protective film 537 may be formed. By combining them, fibrous substance 515 can be formed on arbitrary positions.

The above-mentioned manufacturing method is a simple manufacturing method including a few number of steps. In addition, the above-mentioned manufacturing method uses less expensive silicon wafer instead of expensive SOI wafer, thus enabling a filter device having excellent productivity to be provided.

Sixth Exemplary Embodiment

Hereinafter, a sensor kit using a filter device in accordance with this exemplary embodiment is described with reference to drawings. This exemplary embodiment is different from the preceding exemplary embodiments in that a filter device and a sensor device are integrated with each other to form a sensor kit.

Figure 41:
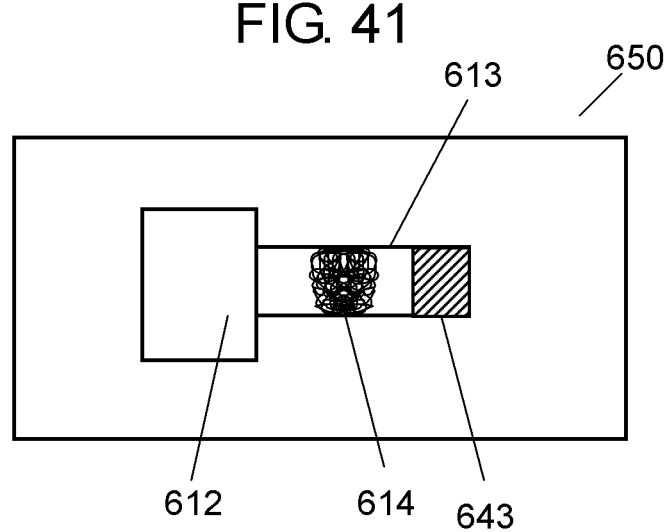
FIG. 41 is a top view of a filter device in accordance with a sixth exemplary embodiment of the present disclosure.
Figure 42:
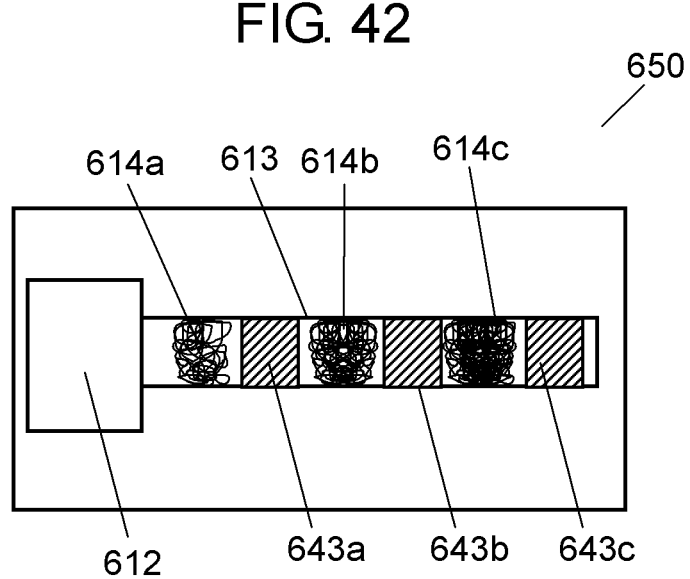
FIG. 42 is a top view of the filter device in accordance with the sixth exemplary embodiment.

FIGS. 41 and 42 are top views each showing a sensor kit in accordance with this exemplary embodiment.

As shown in FIG. 41, sensor kit 650 of this exemplary embodiment includes first port 612 from which a solution containing a substance is to be input, and first flow passage 613 connected to first port 612. First flow passage 613 includes filter portion 614 made of fibrous substances 615 and reaction portion 643 located in the downstream direction from filter portion 614. Since a specimen extracted by filter portion 614 can be examined in reaction portion 613, a specimen extracted by filter portion 514 can be examined simply and at high speed.

For example, when protein, DNA, and the like, are examined, an antibody may be previously disposed in reaction portion 643.

An observation method of reaction is not particularly limited to observation under fluorescence microscope. For example, a SAW (Surface Acoustic Wave) sensor provided with input/output electrode at the both sides of reaction portion 643 is formed, and observation may be carried out by measuring a difference in frequencies between a case in which a specimen is present in reaction portion 643 and a case in which a specimen is not present.

As shown in FIG. 42, filter portion 614 and reaction portion 643 may be alternately formed in first flow passage 613 in sensor kit 650. That is to say, first flow passage 613 includes filter portion 614a, reaction portion 643a, filter portion 614b, reaction portion 643b, filter portion 614c, and reaction portion 643c sequentially from the upstream side. At this time, by, for example, varying filtration products in filter portions 614a, 614b, and 614c, respectively, a plurality of filtration products are filtrated by only one sensor kit, so that different examples can be carried out in reaction portions 643a, 643b, and 643c, respectively.

Filtration products can be varied in filter portions 614a, 614b, and 614c by, for example, reducing gaps of filter portion 614 from the upstream of first flow passage 613, sequentially.

INDUSTRIAL APPLICABILITY

A filter device of the present disclosure is useful for various filter devices such as a separation filter, a disinfect filter, and a particle filter.

REFERENCE MARKS IN DRAWINGS 100, 200, 300, 400, 500, 600 filter device
111, 211 substrate
112, 212, 612 first port
113, 213, 613 first flow passage
114, 214, 314, 414, 514, 614 filter portion
115, 215, 315, 415, 515, 614 fibrous substance
116 branched portion
217 second port
218 second flow passage
219 third port
320 capillary
321, 421, 521 filter chip
322, 422, 522 thin plate
323, 523 first surface
324, 524 second surface
325, 425 through hole 326, 426 holding portion
327 protruding portion
328 recess portion
329 silicon layer
330, 430 silicon dioxide layer
331, 431 silicon layer
332, 532 first resist mask
333, 533 mask hole
334 concave portion
335, 535 second resist mask
336, 536 catalyst layer
337, 537 protective film
338 concave portion
339 convex portion
340 concave and convex portion
541 silicon layer
542 doped layer
643 reaction portion
650 sensor kit

The invention claimed is:

1. A filter device comprising:
a capillary; and
a filter chip provided inside the capillary such that is brought into contact with a solution containing a substance and flowing in the capillary,
wherein the filter chip includes:
a thin plate; and
a through hole which penetrates a first surface at an upper part of the thin plate and a second surface provided opposite to the first surface, and through which the solution flowing in the capillary passes from the first surface to the second surface,
wherein a filter portion made of a plurality of fibrous substances including inorganic oxide is formed at a portion above the through hole so as to cover an opening portion of the through hole opened in the first surface, and the plurality of fibrous substances have one peak in diameter distribution,
wherein the plurality of fibrous substances are entangled with each other, and
wherein the filter portion includes gaps made by the entangled plurality of fibrous substances, and the gaps become narrower toward a downstream of the capillary.

2. The filter device of claim 1,
wherein the plurality of fibrous substances are formed also on an inner wall of the through hole.

3. The filter device of claim 1,
wherein a holding portion is formed on the first surface of the thin plate.

4. The filter device of claim 3,
wherein the holding portion is provided with a taper such that a region surrounded by the holding portion becomes narrower from an upper surface toward the thin plate.

5. The filter device of claim 3,
wherein the plurality of fibrous substances are formed in a region surrounded by the holding portion.

6. The filter device of claim 3,
wherein at least one or more protruding portions are provided on an inner wall of the holding portion.

7. The filter device of claim 3,
wherein at least one or more acute-angled recess portions are provided on an inner wall of the holding portion.

8. The filter device of claim 1,
wherein the thin plate includes a boron-doped silicon layer.

9. The filter device of claim 1,
wherein an outer wall surface of the filter chip includes concave and convex shapes.

10. The filter device of claim 1,
wherein the capillary includes a plurality of the filter chips inside thereof.

11. The filter device of claim 1, wherein:
a silicon-on-insulator (SOI) substrate is used as a base material for forming the filter chip, and
the plurality of fibrous substances and a silicon layer of the SOI substrate are directly joined to each other.

12. The filter device of claim 1,
wherein the plurality of fibrous substances are entangled with each other, and a size of gaps made by the entangled plurality of fibrous substances is 3 μm to 6 μm.

13. The filter device of claim 1,
wherein gaps lade by the plurality of fibrous substances have an aspect ratio of not less than 2.

14. The filter device of claim 1,
wherein a diameter distribution of the plurality of fibrous substances is continuous normal distribution when the range of the diameter of the plurality of fibrous substances is less than twice standard deviation of the diameter of the plurality of fibrous substances.

15. The filter device of claim 1,
wherein a diameter distribution of the plurality of fibrous substances is continuous normal distribution when the diameter distribution is drawn with an interval of the diameter of the plurality of fibrous substances which is less than standard deviation of the diameter of the plurality of fibrous substances.

16. The filter device of claim 1,
wherein a concavity or a convexity is formed on the first surface.

17. The filter device of claim 1, wherein:
the thin plate includes a plurality of through holes, and
an interval between the plurality of through holes is not smaller than 10 μm.

18. The filter device of claim 16, wherein:
the thin plate includes a plurality of through holes, and
the plurality of through holes are arranged in such a manner that they are not along a cleavage plane.

19. The filter device of claim 1, wherein:
the thin plate includes a plurality of through holes, and
a concave portion is formed at the opening portion of each of the plurality of through holes on the first surface.

20. The filter device of claim 19,
wherein the through hole is provided with a taper such that a diameter of through hole becomes smaller from the first surface to the second surface.

21. The filter device of claim 1,
wherein a protective film is formed on an inner wall of the through hole.

22. The filter device of claim 1,
wherein a protective film is formed on a rear surface of the thin plate.

23. The filter device of claim 21,
wherein a square mean roughness of a surface of the protective film is not more than 5.0 nm.

24. The filter device of claim 21, wherein:
the protective film is further formed on a rear surface of the thin plate, and
a square mean roughness of a surface of the protective film is not more than 5.0 nm.

* * * * *